US010723773B2

(12) United States Patent
Schmidt et al.

(10) Patent No.: US 10,723,773 B2
(45) Date of Patent: *Jul. 28, 2020

(54) RECOMBINANT LUBRICIN

(71) Applicant: Lubris LLC, Framingham, MA (US)

(72) Inventors: Tannin A. Schmidt, West Hartford, CT (US); Gregory D. Jay, Norfolk, MA (US)

(73) Assignee: Lubris LLC, Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/183,497

(22) Filed: Nov. 7, 2018

(65) Prior Publication Data

US 2019/0270783 A1 Sep. 5, 2019

Related U.S. Application Data

(63) Continuation of application No. 15/030,825, filed as application No. PCT/US2014/061827 on Oct. 22, 2014, now Pat. No. 10,125,180.

(60) Provisional application No. 61/894,366, filed on Oct. 22, 2013.

(51) Int. Cl.
C07K 14/475 (2006.01)
C07K 14/47 (2006.01)
A61K 9/00 (2006.01)
A61K 31/728 (2006.01)
A61K 47/36 (2006.01)
A61K 38/17 (2006.01)
C12P 21/00 (2006.01)

(52) U.S. Cl.
CPC .......... C07K 14/4725 (2013.01); A61K 9/008 (2013.01); A61K 9/0014 (2013.01); A61K 9/0019 (2013.01); A61K 9/0048 (2013.01); A61K 31/728 (2013.01); A61K 38/1709 (2013.01); A61K 47/36 (2013.01); C12P 21/005 (2013.01)

(58) Field of Classification Search
CPC .................................................. C07K 14/4725
See application file for complete search history.

(56) References Cited

U.S. PATENT DOCUMENTS

| 6,743,774 | B1 | 6/2004 | Jay |
| 6,960,562 | B2 | 11/2005 | Jay |
| 7,001,881 | B1 | 2/2006 | Jay |
| 7,129,062 | B2 | 10/2006 | Mermod et al. |
| 7,415,381 | B2 | 8/2008 | Jay |
| 7,618,941 | B2 | 11/2009 | Jay |
| 7,642,236 | B2 | 1/2010 | Flannery et al. |
| 7,893,029 | B2 | 2/2011 | Flannery et al. |
| 8,026,346 | B2 | 9/2011 | Jay |
| 8,252,917 | B2 | 8/2012 | Mermod et al. |
| 8,506,944 | B2 | 8/2013 | Sullivan et al. |
| 8,551,467 | B2 | 10/2013 | Sullivan et al. |
| 8,563,028 | B2 | 10/2013 | Sullivan et al. |
| 8,680,057 | B2 | 3/2014 | Jay |
| 8,795,723 | B2 | 8/2014 | Gervais et al. |
| 8,945,604 | B2 | 2/2015 | Sullivan et al. |
| 8,980,840 | B2 | 3/2015 | Truitt, III et al. |
| 9,107,885 | B2 | 8/2015 | Sullivan et al. |
| 9,138,457 | B2 | 9/2015 | Sullivan et al. |
| 9,248,161 | B2 | 2/2016 | Sullivan et al. |
| 9,393,285 | B2 | 7/2016 | Sullivan et al. |
| 9,421,241 | B2 | 8/2016 | Sullivan et al. |
| 9,585,936 | B2 | 3/2017 | Sullivan et al. |
| 9,730,865 | B2 | 8/2017 | Sullivan et al. |
| 9,730,978 | B2 | 8/2017 | Sullivan et al. |
| 10,125,180 | B2 * | 11/2018 | Schmidt ............. A61K 38/1709 |
| 2003/0087342 | A1 | 5/2003 | Mermod et al. |
| 2004/0072741 | A1 | 4/2004 | Jay |
| 2004/0229804 | A1 | 11/2004 | Jay |
| 2006/0240037 | A1 | 10/2006 | Fey et al. |
| 2007/0111327 | A1 | 5/2007 | Jay |
| 2007/0249557 | A1 | 10/2007 | Jay |
| 2008/0139458 | A1 | 6/2008 | Jay et al. |
| 2008/0287369 | A1 | 11/2008 | Jay |
| 2009/0068247 | A1 | 3/2009 | Jay |
| 2009/0104148 | A1 | 4/2009 | Jay et al. |
| 2009/0155200 | A1 | 6/2009 | Jay |
| 2010/0098749 | A1 | 4/2010 | Barenholz et al. |
| 2010/0204087 | A1 | 8/2010 | Jay |
| 2011/0059902 | A1 | 3/2011 | Sullivan et al. |

(Continued)

FOREIGN PATENT DOCUMENTS

WO WO-1998/008934 A1 3/1998
WO WO-2005/102363 A2 11/2005

(Continued)

OTHER PUBLICATIONS

"Selexis Lubris Partnership Advances Difficult-to-Express Protein Towards Clinic," Selexis Archived Press Release, Jun. 27, 2012 (Jun. 27, 2012), pp. 1-2. Retrieved from the Internet: www.selexis.com/#!12-selexis-lubris-partnership/ctty <http://www.selexis.com/#!12-selexis-lubris-partnership/ctty> on Jan. 16, 2015 (Jan. 16, 2015). entire document.

Abubacker S et al., (2016), 'Full-Length Recombinant Human Proteoglycan 4 Interacts with Hyaluronan to Provide Cartilage Boundary Lubrication,' Ann Biomed Eng, 44(4):1128-37.

Ali et al., (2014) "The O-glycomap of Lubricin, a Novel Mucin Responsible for Joint Lubrication, Identified by Site-specific Glycopeptide Analysis", Molecular & Cellular Proteomics 13: 10.1074/mcp.M114.040865, 3396-3409, 2014.

Appendix 1B: Symbol Nomenclature for Glycans (SNFG) in Essentials of Glycobiology, 3rd Ed. Varki et al., eds., 2015-2017, Cold Springs Harbor Laboratory Press: Cold Spring Harbor, NY, (1 page).

(Continued)

Primary Examiner — Prema M Mertz
(74) Attorney, Agent, or Firm — Goodwin Procter LLP

(57) ABSTRACT

Disclosed are new recombinant isoforms of human-like lubricin or PRG4 glycoprotein having outstanding lubrication properties and a novel glycosylation pattern, and methods for their manufacture at high levels enabling commercial production.

10 Claims, 19 Drawing Sheets
Specification includes a Sequence Listing.

(56) References Cited

U.S. PATENT DOCUMENTS

| | | | |
|---|---|---|---|
| 2011/0061117 | A1 | 3/2011 | Mermod et al. |
| 2011/0142908 | A1 | 6/2011 | Sullivan et al. |
| 2012/0052077 | A1 | 3/2012 | Truitt, III et al. |
| 2012/0134925 | A1 | 5/2012 | Sullivan et al. |
| 2012/0231449 | A1 | 9/2012 | Mermod et al. |
| 2012/0321611 | A1 | 12/2012 | Sullivan et al. |
| 2012/0321693 | A1 | 12/2012 | Sullivan et al. |
| 2013/0039865 | A1 | 2/2013 | Truitt, III et al. |
| 2013/0116186 | A1 | 5/2013 | Jay |
| 2013/0143264 | A1 | 6/2013 | Nicolas et al. |
| 2013/0196930 | A1 | 8/2013 | Flannery et al. |
| 2013/0315973 | A1 | 11/2013 | Jay |
| 2014/0179611 | A1 | 6/2014 | Jay |
| 2016/0235809 | A1 | 8/2016 | Sullivan et al. |
| 2016/0250286 | A1 | 9/2016 | Schmidt |
| 2017/0312335 | A1 | 11/2017 | Truitt, III et al. |
| 2018/0140546 | A1 | 5/2018 | Sullivan et al. |
| 2018/0161393 | A1 | 6/2018 | Jay et al. |

FOREIGN PATENT DOCUMENTS

| | | | |
|---|---|---|---|
| WO | WO-2006/012492 | A2 | 2/2006 |
| WO | WO-2008/143816 | A1 | 11/2008 |
| WO | WO-2015/061488 | A1 | 4/2015 |
| WO | WO-2015/081121 | A1 | 6/2015 |
| WO | WO-2016/123123 | A1 | 8/2016 |
| WO | WO-2016/187414 | A1 | 11/2016 |

OTHER PUBLICATIONS

Brockhausen et al., Chapter 10: O-GalNAc Glycans in "Essentials of Glycobiology, 3rd Ed." Varki et al., eds., 2015-2017, Cold Springs Harbor Laboratory Press: Cold Spring Harbor, NY, (20 pages).

Brockhausen I et al., 'Chapter 9. O-GalNAc Glycans,' *Essentials of Glycobiology* (2nd Ed, 2009), A Varki et al., (Eds), Cold Spring Harbor Laboratory Press, Cold Spring, NY (Pub), pp. 115-127 (retrieved from the internet at <http://www.ncbi.nim.nih.gov/books/NBK1896 on Jan. 16, 2015>).

Dorosz S et al., (2003), 'Cartilage Boundary Lubricating Ability of Full-Length Human Recombinant PRG4—Alone and in Combination with Hyaluronan,' 59th Annual Meeting of the Orthopaedic Research Society, San Antonio, TX, Jan. 26-29, 2013, Poster No. 1276, University of Calgary, Calgary, Canada (Pub) (Poster).

Dorosz S et al., (2003), 'Cartilage Boundary Lubricating Ability of Full-Length Human Recombinant PRG4—Alone and in Combination with Hyaluronan,' 59th Annual Meeting of the Orthopaedic Research Society, San Antonio, TX, Jan. 26-29, 2013, Session No. PS2-063, vol. No. 38, Paper No. 1276, Orthopaedic Research Society, Rosemont, IL (Pub) (2 pages) (Poster 1276).

Estrella RP et al., (2010), 'The Glycosylation of Human Synovial Lubricin: Implications for its Role in Inflammation,' Biochem J, 429(2):359-67.

Flannery et al., "Prevention of Cartilage Degeneration in a Rat Model of Osteoarthritis by Intraarticular Treatment with Recombinant Lubricin", Arthritis & Rheumatism, American College of Rheumatology, Mar. 3, 2009, vol. 60, No. 3, pp. 840-847.

Girod PA et al., (2007), 'Genome-wide Prediction of Matrix Attachment Regions that Increase Gene Expression in Mammalian Cells,' Nat Methods, 4(9):747-53.

Gleghorn JP et al., (2009), 'Boundary Mode Lubrication of Articular Cartilage by Recombinant Human Lubricin,' J Orthop Res, 27(6):771-7.

Harraghy N et al., (2008), 'Sustained Transgene Expression Using MAR Elements,' Curr Gene Ther, 8(5):353-66.

Hart CM and Laemmli UK, (1998), 'Facilitation of Chromatin Dynamics by SARs,' Curr Opin Genet Dev, 8(5):519-25.

Ikegawa S et al., (2000), 'Isolation Characterization and Mapping of the Mouse and Human PRG4 (Proteoglycan 4) Genes,' Cytogenet Cell Genet, 90(3-4):291-7.

International Search Report (Form ISA/201) for International Application No. PCT/US2014/061827 dated Feb. 5, 2015 (4 pages).

Jay GD et al, Homology of lubricin and superficial zone protein (SZP): products of megakaryocyte stimulating factor (MSF) gene expression by human synovial fibroblasts and articular chondrocytes localized to chromosome 1q25. J Orthop Res, Jul. 31, 2001, vol. 19, No. 4, pp. 677-687.

Jay GD et al., (2001), 'Boundary Lubrication by Lubricin is Mediated by O-Linked β(1-3)Gal-GalNAc Oligosaccharides,' Glycoconj J, 18(10):807-15.

Jay GD et al., (2007), 'Association Between Friction and Wear in Diarthrodial Joints Lacking Lubricin,' Arthritis Rheum, 56(11):3662-9.

Jay GD et al., (2010), 'Prevention of Cartilage Degeneration and Restoration of Chondroprotection by Lubricin Tribosupplementation in the Rat Following Anterior Cruciate Ligament Transection,' Arthritis Rheum, 62(8):2382-91.

Jay GD, (2004), 'Lubricin and Surfacing of Articular Joints,' Curr Opin Orthop, 15(5):355-9.

Jenuwein T et al., (1997), 'Extension of Chromatin Accessibility by Nuclear Matrix Attachment Regions,' Nature, 385(6613):269-72.

Jones ARC et al., (2002), 'Degradation of PRG4/SZP by Matrix Proteases,' 49th Annual Meeting of the Orthopaedic Reserach Study, Paper #0133, 1 page.

Jones ARC et al., (2007), 'Binding and Localization of Recombinant Lubricin to Articular Cartilage Surfaces,' J Orthop Res, 25(3):283-92.

Kooyman J et al., (2010), 'Cartilage Boundary Lubricating Properties of Native Proteoglycan 4 Purified from Normal Bovin Synovial Fluid,' 56th Annual Meeting of the Orthopaedic Research Society, New Orleans, LA, Mar. 6-10, 2010, vol. No. 35, Paper No. 255, Orthopaedic Research Society, Rosemont, IL (Pub) (1 page).

Könitzer, (2015), "A global RNA-seq-driven analysis of CHO host and production cell lines reveals distinct differential expression patterns of genes contributing to recombinant antibody glycosylation", Biotechnol. J., 10:1412-1423.

Le Fourn et al., (2014), "CHO Cell engineering to prevent polypeptide aggregation and improve therapeutic protein secretion," Metabolic Engineering 21:91-102.

Lee DW et al., (2013), 'Stick-Slip Friction and Wear of Articular Joints,' Proc Natl Acad Sci USA, 110(7):E567-74.

Ludwig TE et al., (2012), 'Diminished Cartilage-Lubricating Ability of Human Osteoarthritic Synovial Fluid Deficient in Proteoglycan 4 Restoration Through Proteoglycan 4 Supplementation,' Arthritis Rheum, 64(12):3963-71.

Schmidt TA et al., (2007), 'Boundary Lubrication of Articular Cartilage Role of Synovial Fluid Constituents,' Arthritis Rheum, 56(3):882-91.

Schmidt TA et al., (2009), 'Disulfide-Bonded Multimers of Proteoglycan 4 PRG-4 are Present in Normal Synovial Fluids,' Biochim Biophys Acta, 1790(5):375-84.

Supplementary European Search Report for European Patent No. EP14856188, dated Apr. 6, 2017, 3 pages.

Written Opinion of the International Searching Authority (Form ISA/237) for International Application No. PCT/US2014/061827 dated Feb. 5, 2015 (7 pages).

Yang et al., (2014), "The GalNAc-type OGlycoproteome of CHO Cells Characterized by the Simple Cell Strategy", Molecular & Cellular Proteomics, 13:3224-3225.

\* cited by examiner

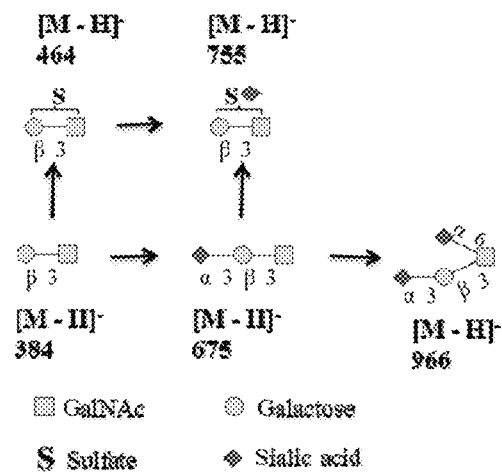
FIG. 6 - glycosylation (recombinant)
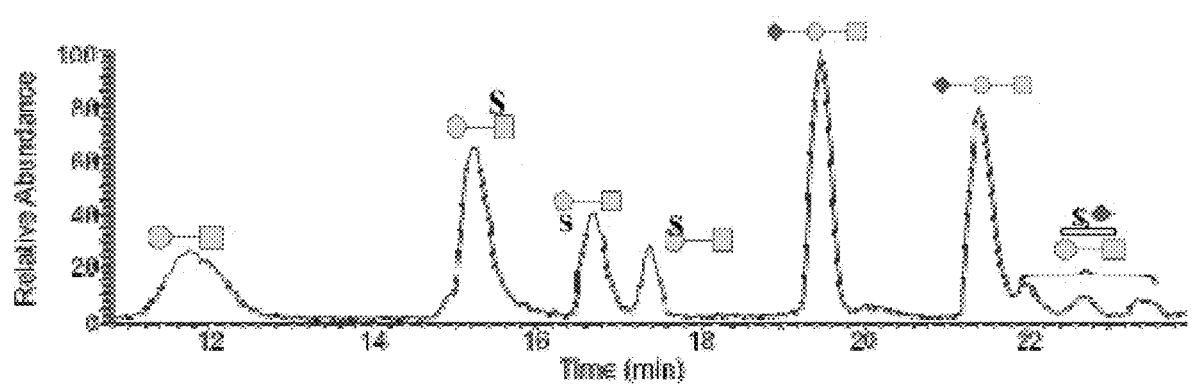
FIG. 7 - glycosylation (recombinant)

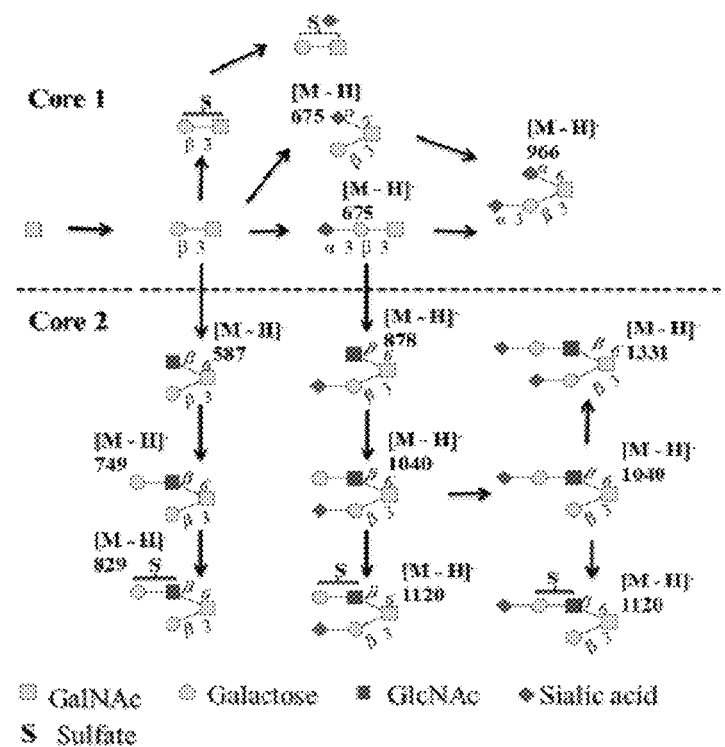
FIG. 8 - glycosylation (native)
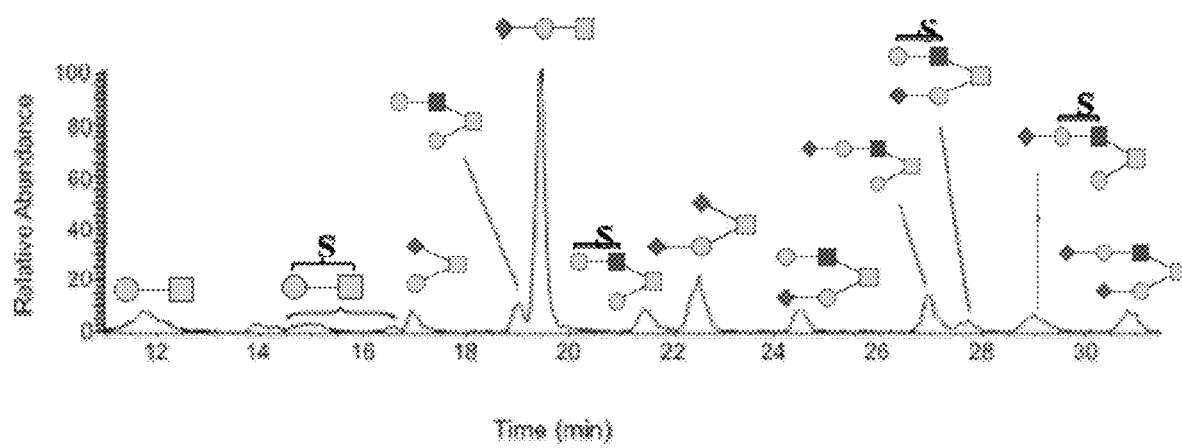
FIG. 9 - glycosylation (native)

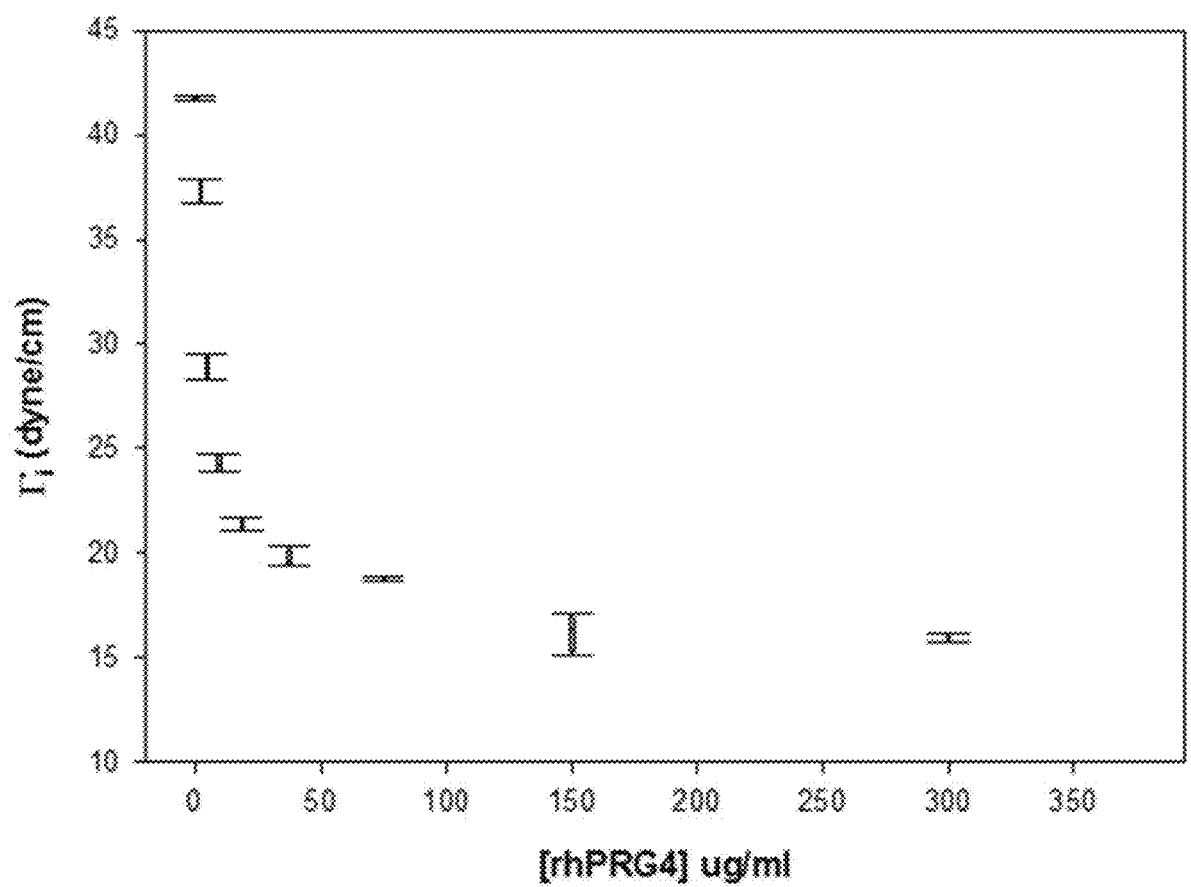
FIG. 10A rhPRG4 Surfactant Properties

FIG. 15

SEQ ID NO: 1, LENGTH: 1404, ORGANISM: Homo sapiens, UniProt Accession No. Q92954:

MAWKTLPIYL LLLLSVFVIQ QVSSQDLSSC AGRCGEGYSR DATCNCDYNC QHYMECCPDF
KRVCTAELSC KGRCFESFER GRECDCDAQC KKYDKCCPDY ESFCAEVHNP TSPPSSKKAP
PPSGASQTIK STTKRSPKPP NKKKTKKVIE SEEITEEHSV SENQESSSSS SSSSSSSTIR
KIKSSKNSAA NRELQKKLKV KDNKKNRTKK KPTPKPPVVD EAGSGLDNGD FKVTTPDTST
TQHNKVSTSP KITTAKPINP RPSLPPNSDT SKETSLTVNK ETTVETKETT TTNKQTSTDG
KEKTTSAKET QSIEKTSAKD LAPTSKVLAK PTPKAETTTK GPALTTPKEP TPTTPKEPAS
TTPKEPTPTT IKSAPTTPKE PAPTTTKSAP TTPKEPAPTT TKEPAPTTPK EPAPTTTKEP
APTTTKSAPT TPKEPAPTTP KKPAPTTPKE PAPTTPKEPT PTTPKEPAPT TKEPAPTTPK
EPAPTAPKKP APTTPKEPAP TTPKEPAPTT TKEPSPTTPK EPAPTTTKSA PTTTKEPAPT
TTKSAPTTPK EPSPTTTKEP APTTPKEPAP TTPKKPAPTT PKEPAPTTPK EPAPTTTKKP
APTTPKEPAP TTPKETAPTT PKKLTPTTPE KLAPTTPEKP APTTPEELAP TTPEEPTPTT
PEEPAPTTPK AAAPNTPKEP APTTPKEPAP TTPKEPAPTT PKETAPTTPK GTAPTTLKEP
APTTPKKPAP KELAPTTTKE PTSTTCDKPA PTTPKGTAPT TPKEPAPTTP KEPAPTTPKG
TAPTTLKEPA PTTPKKPAPK ELAPTTTKGP TSTTSDKPAP TTPKETAPTT PKEPAPTTPK
KPAPTTPETP PPTTSEVSTP TTTKEPTTIH KSPDESTPEL SAEPTPKALE NSPKEPGVPT
TKTPAATKPE MTTTAKDKTT ERDLRTTPET TTAAPKMTKE TATTTEKTTE SKITATTTQV
TSTTTQDTTP FKITTLKTTT LAPKVTTTKK TITTTEIMNK PEETAKPKDR ATNSKATTPK
PQKPTKAPKK PTSTKKPKTM PRVRKPKTTP TPRKMTSTMP ELNPTSRIAE AMLQTTTRPN
QTPNSKLVEV NPKSEDAGGA EGETPHMLLR PHVFMPEVTP DMDYLPRVPN QGIIINPMLS
DETNICNGKP VDGLTTLRNG TLVAFRGHYF WMLSPFSPPS PARRITEVWG IPSPIDTVFT
RCNCEGKTFF FKDSQYWRFT NDIKDAGYPK PIFKGFGGLT GQIVAALSTA KYKNWPESVY
FFKRGGSIQQ YIYKQEPVQK CPGRRPALNY PVYGETTQVR RRFERAIGP SQTHTIRIQY
SPARLAYQDK GVLHNEVKVS ILWRGLPNVV TSAISLPNIR KPDGYDYYAF SKDQYYNIDV
PSRTARAITT RSGQTLSKVW YNCP

FIG. 16

SEQ ID NO: 2 LENGTH: 5041, TYPE: DNA, ORGANISM: Homo sapiens, GenBank Accession No. U70136.1:

GCGGCCGCGACTATTCGGTACCTGAAAACAACGATGGCATGGAAAACACTTCCCATTTACCTGT
TGTTGCTGCTGTCTGTTTTCGTGATTCAGCAAGTTTCATCTCAAGATTTATCAAGCTGTGCAGG
GAGATGTGGGGAAGGGTATTCTAGAGATGCCACCTGCAACTGTGATTATAACTGTCAACACTAC
ATGGAGTGCTGCCCTGATTTCAAGAGAGTCTGCACTGCGGAGCTTTCCTGTAAAGGCCGCTGCT
TTGAGTCCTTCGAGAGAGGGAGGGAGTGTGACTGCGACGCCCAATGTAAGAAGTATGACAAGTG
CTGTCCCGATTATGAGAGTTTCTGTGCAGAAGTGCATAATCCCACATCACCACCATCTTCAAAG
AAAGCACCTCCACCTTCAGGAGCATCTCAAACCATCAAATCAACAACCAAACGTTCACCCAAAC
CACCAAACAAGAAGAAGACTAAGAAAGTTATAGAATCAGAGGAAATAACAGAAGAACATTCTGT
TTCTGAAAATCAAGAGTCCTCCTCCTCCTCCTCCTCTTCCTCTTCTTCTTCAACAATTTGGAAA
ATCAAGTCTTCCAAAAATTCAGCTGCTAATAGAGAATTACAGAAGAAACTCAAAGTAAAAGATA
ACAAGAAGAACAGAACTAAAAAGAAACCTACCCCAAACCACCAGTTGTAGATGAAGCTGGAAG
TGGATTGGACAATGGTGACTTCAAGGTCACAACTCCTGACACGTCTACCACCCAACACAATAAA
GTCAGCACATCTCCCAAGATCACAACAGCAAAACCAATAAATCCCAGACCCAGTCTTCCACCTA
ATTCTGATACATCTAAAGAGACGTCTTTGACAGTGAATAAAGAGACAACAGTTGAAACTAAAGA
AACTACTACAACAAATAAACAGACTTCAACTGATGGAAAAGAGAAGACTACTTCCGCTAAAGAG
ACACAAAGTATAGAGAAAACATCTGCTAAAGATTTAGCACCCACATCTAAAGTGCTGGCTAAAC
CTACACCCAAAGCTGAAACTACAACCAAAGGCCCTGCTCTCACCACTCCCAAGGAGCCCACGCC
CACCACTCCCAAGGAGCCTGCATCTACCACACCCAAAGAGCCCACACCTACCACCATCAAGTCT
GCACCCACCACCCCCAAGGAGCCTGCACCCACCACCACCAAGTCTGCACCCACCACTCCCAAGG
AGCCTGCACCCACCACCACCAAGGAGCCTGCACCCACCACTCCCAAGGAGCCTGCACCCACCAC
CACCAAGGAGCCTGCACCCACCACCACCAAGTCTGCACCCACCACTCCCAAGGAGCCTGCACCC
ACCACCCCAAGAAGCCTGCCCCAACTACCCCAAGGAGCCTGCACCCACCACTCCCAAGGAGC
CTACACCCACCACTCCCAAGGAGCCTGCACCCACCACCAAGGAGCCTGCACCCACCACTCCCAA
AGAGCCTGCACCCACTGCCCCCAAGAAGCCTGCCCCAACTACCCCAAGGAGCCTGCACCCACC
ACTCCCAAGGAGCCTGCACCCACCACCACCAAGGAGCCTTCACCCACCACTCCCAAGGAGCCTG
CACCCACCACCACCAAGTCTGCACCCACCACTACCAAGGAGCCTGCACCCACCACTACCAAGTC
TGCACCCACCACTCCCAAGGAGCCTTCACCCACCACCACCAAGGAGCCTGCACCCACCACTCCC

FIGURE 16 (CONTINUED)

AAGGAGCCTGCACCCACCACCCCCAAGAAGCCTGCCCCAACTACCCCCAAGGAGCCTGCACCCA
CCACTCCCAAGGAACCTGCACCCACCACCACCAAGAAGCCTGCACCCACCGCTCCCAAAGAGCC
TGCCCCAACTACCCCCAAGGAGACTGCACCCACCACCCCCAAGAAGCTCACGCCCACCACCCC
GAGAAGCTCGCACCCACCACCCCTGAGAAGCCCGCACCCACCACCCCTGAGGAGCTCGCACCCA
CCACCCCTGAGGAGCCCACACCCACCACCCCTGAGGAGCCTGCTCCCACCACTCCCAAGGCAGC
GGCTCCCAACACCCCTAAGGAGCCTGCTCCAACTACCCCTAAGGAGCCTGCTCCAACTACCCCT
AAGGAGCCTGCTCCAACTACCCCTAAGGAGACTGCTCCAACTACCCCTAAAGGGACTGCTCCAA
CTACCCTCAAGGAACCTGCACCCACTACTCCCAAGAAGCCTGCCCCAAGGAGCTTGCACCCAC
CACCACCAAGGAGCCCACATCCACCACCTCTGACAAGCCCGCTCCAACTACCCCTAAGGGGACT
GCTCCAACTACCCCTAAGGAGCCTGCTCCAACTACCCCTAAGGAGCCTGCTCCAACTACCCCTA
AGGGGACTGCTCCAACTACCCTCAAGGAACCTGCACCCACTACTCCCAAGAAGCCTGCCCCCAA
GGAGCTTGCACCCACCACCACCAAGGGGCCCACATCCACCACCTCTGACAAGCCTGCTCCAACT
ACACCTAAGGAGACTGCTCCAACTACCCCCAAGGAGCCTGCACCCACTACCCCCAAGAAGCCTG
CTCCAACTACTCCTGAGACACCTCCTCCAACCACTTCAGAGGTCTCTACTCCAACTACCACCAA
GGAGCCTACCACTATCCACAAAAGCCCTGATGAATCAACTCCTGAGCTTTCTGCAGAACCCACA
CCAAAAGCTCTTGAAAACAGTCCCAAGGAACCTGGTGTACCTACAACTAAGACTCCTGCAGCGA
CTAAACCTGAAATGACTACAACAGCTAAAGACAAGACAACAGAAAGAGACTTACGTACTACACC
TGAAACTACAACTGCTGCACCTAAGATGACAAAAGAGACAGCAACTACAACAGAAAAAACTACC
GAATCCAAAATAACAGCTACAACCACACAAGTAACATCTACCACAACTCAAGATACCACACCAT
TCAAAATTACTACTCTTAAAACAACTACTCTTGCACCCAAAGTAACTACAACAAAAAAGACAAT
TACTACCACTGAGATTATGAACAAACCTGAAGAAACAGCTAAACCAAAAGACAGAGCTACTAAT
TCTAAAGCGACAACTCCTAAACCTCAAAAGCCAACCAAAGCACCCAAAAAACCCACTTCTACCA
AAAAGCCAAAAACAATGCCTAGAGTGAGAAAACCAAAGACGACACCAACTCCCCGCAAGATGAC
ATCAACAATGCCAGAATTGAACCCTACCTCAAGAATAGCAGAAGCCATGCTCCAAACCACCACC
AGACCTAACCAAACTCCAAACTCCAAACTAGTTGAAGTAAATCCAAAGAGTGAAGATGCAGGTG
GTGCTGAAGGAGAAACACCTCATATGCTTCTCAGGCCCCATGTGTTCATGCCTGAAGTTACTCC
CGACATGGATTACTTACCGAGAGTACCCAATCAAGGCATTATCATCAATCCCATGCTTTCCGAT
GAGACCAATATATGCAATGGTAAGCCAGTAGATGGACTGACTACTTTGCGCAATGGGACATTAG
TTGCATTCCGAGGTCATTATTTCTGGATGCTAAGTCCATTCAGTCCACCATCTCCAGCTCGCAG

FIGURE 16 (CONTINUED)

```
AATTACTGAAGTTTGGGGTATTCCTTCCCCCATTGATACTGTTTTACTAGGTGCAACTGTGAA
GGAAAAACTTTCTTCTTTAAGGATTCTCAGTACTGGCGTTTTACCAATGATATAAAAGATGCAG
GGTACCCCAAACCAATTTTCAAAGGATTTGGAGGACTAACTGGACAAATAGTGGCAGCGCTTTC
AACAGCTAAATATAAGAACTGGCCTGAATCTGTGTATTTTTTCAAGAGAGGTGGCAGCATTCAG
CAGTATATTTATAAACAGGAACCTGTACAGAAGTGCCCTGGAAGAAGGCCTGCTCTAAATTATC
CAGTGTATGGAGAAATGACACAGGTTAGGAGACGTCGCTTTGAACGTGCTATAGGACCTTCTCA
AACACACACCATCAGAATTCAATATTCACCTGCCAGACTGGCTTATCAAGACAAAGGTGTCCTT
CATAATGAAGTTAAAGTGAGTATACTGTGGAGAGGACTTCCAAATGTGGTTACCTCAGCTATAT
CACTGCCCAACATCAGAAAACCTGACGGCTATGATTACTATGCCTTTTCTAAAGATCAATACTA
TAACATTGATGTGCCTAGTAGAACAGCAAGAGCAATTACTACTCGTTCTGGGCAGACCTTATCC
AAAGTCTGGTACAACTGTCCTTAGACTGATGAGCAAAGGAGGAGTCAACTAATGAAGAAATGAA
TAATAAATTTTGACACTGAAAAACATTTTATTAATAAAGAATATTGACATGAGTATACCAGTTT
ATATATAAAATGTTTTTAAACTTGACAATCATTACACTAAAACAGATTTGATAATCTTATTCA
CAGTTGTTATTGTTTACAGACCATTTAATTAATATTTCCTCTGTTTATTCCTCCTCTCCCTCCC
ATTGCATGGCTCACACCTGTAAAGAAAAAGAATCAAATTGAATATATCTTTTAAGAATTCAA
AACTAGTGTATTCACTTACCCTAGTTCATTATAAAAAATATCTAGGCATTGTGGATATAAAACT
GTTGGGTATTCTACAACTTCAATGGAAATTATTACAAGCAGATTAATCCCTCTTTTTGTGACAC
AAGTACAATCTAAAAGTTATATTGGAAAACATGGAAATATTAAAATTTTACACTTTTACTAGCT
AAAACATAATCACAAAGCTTTATCGTGTTGTATAAAAAAATTAACAATATAATGGCAATAGGTA
GAGATACAACAAATGAATATAACACTATAACACTTCATATTTTCCAAATCTTAATTTGGATTTA
AGGAAGAAATCAATAAATATAAAATATAAGCACATATTTATTATATATCTAAGGTATACAAATC
TGTCTACATGAAGTTTACAGATTGGTAAATATCACCTGCTCAACATGTAATTATTTAATAAAAC
TTTGGAACATTAAAAAAATAAATTGGAGGCTTAAAAAAAAAAAAAAAAA
```

| |  |  |  |  |  |
|---|---:|---:|---:|---:|---:|
| Glycan | 384 | 464 | 675 | 755 | 966 |
| Percentage | 19.8 | 34.3 | 33.2 | 12.1 | 0.6 |
FIGURE 17

RECOMBINANT LUBRICIN

CROSS-REFERENCE TO RELATED APPLICATIONS

This application is a continuation of U.S. patent application Ser. No. 15/030,825, filed Apr. 20, 2016, which is a U.S. national stage application filed under 35 U.S.C. § 371 of International Patent Application No. PCT/US2014/061827, filed Oct. 22, 2014, which claims priority to and the benefit of U.S. Provisional Patent Application No. 61/894,366 filed Oct. 22, 2013, the contents of each application being incorporated by reference herein in their entireties.

FIELD OF THE INVENTION

The inventions disclosed herein relate to methods of producing commercial quantities of compositions of matter comprising recombinant human-like lubricin using transfected cells. More particularly, the inventions relate to production at commercial scale of novel forms of lubricin which have excellent lubricating properties and which may be formulated and used for prophylactically or therapeutically treating various conditions ranging, for example, from joint pain to dry eye disease.

BACKGROUND OF THE INVENTION

The proteoglycan 4 (PRG4) gene encodes highly glycosylated surface lubricating proteins named lubricin, megakaryocyte stimulating factor (MSF), or superficial zone protein (SZP). (See Jay, Curr. Opin. Orthop. 15, 355 (2004); U.S. Pat. Nos. 6,743,774; 6,960,562). Lubricin is expressed from the PRG4 gene (SEQ ID NO: 2) with a full length spanning 12 exons, although multiple, naturally occurring truncated versions have been reported. A large "mucin like" central domain of 940 amino acids (encoded by exon 6) comprises some 70+ KEPAPTT (SEQ ID NO:3)-like sequences and is glycosylated heavily. The glycoprotein comprises core 2 glycosylation residues and a multiplicity of core 1 glycans (O-linked β (1-3) Gal-GalNAc oligosaccharides), at least the latter of which have been shown to mediate its primary physiological function, boundary lubrication (Jay et al., Glycoconj J 18, 807 (2001)). PRG4 has been shown to be present at the surface of cartilage, synovium, tendon, and meniscus, in the tear film and at other anatomical sites. PRG4 has been shown to contribute to the boundary lubrication of apposing articular cartilage surfaces. PRG4 has been shown to exist not only as a monomer but also as a dimer and multimer disulfide-bonded through the conserved cysteine-rich domains at both N- and C-termini, (Schmidt et al., Biochim Biophys Acta. 1790(5):375-84 (2009); Kooyman et al., Paper No. 255, 56$^{th}$ Ann. Meet of Orthop. Res. Soc., 2010).

At the cartilage interface of synovial joints there are at least two physicochemical modes of lubrication in action. These have been classified as "fluid film" and "boundary." The operative lubrication modes depend on the normal and tangential forces on the articulating tissues, on the relative rate of tangential motion between these surfaces, and on the time history of both loading and motion. The friction coefficient, $\mu$ (a dimensionless unit, ratio of the measured frictional force between two contacting surfaces in relative motion to the applied normal force), provides a quantitative measure of lubrication.

One type of fluid-mediated lubrication or "fluid film" mode is hydrostatic. At the onset of loading and typically for a prolonged duration, the interstitial fluid within cartilage becomes pressurized, due to the biphasic nature of the tissue, fluid may also be forced into the asperities between articular surfaces through a weeping mechanism. Pressurized interstitial fluid and trapped lubricant pools comprising hyaluronic acid may therefore contribute significantly to the bearing of normal load with little resistance to shear force, facilitating a very low friction coefficient. Also, at the onset of loading and/or motion, squeeze film, hydrodynamic, and elastohydrodynamic types of fluid film lubrication may occur, with pressurization, motion, and deformation acting to drive viscous lubricant from and/or through the gap between two surfaces in relative motion.

In boundary lubrication, load is supported by surface-to-surface contact, and the associated frictional properties are determined by lubricant surface molecules, i.e., lubricin species. This mode is important because the opposing cartilage layers make contact over +/−10% of the total area via interlocking, flattened asperities, and this likely is where most of the friction occurs. Boundary lubrication, in essence, mitigates "stick-slip" (Meyer et al., Nanoscience: Friction and Rheology on the Nanometer Scale, World Scientific Publishing Co. Pte. Ltd, River Edge, N.J., (2002), pp. 373), that is, spontaneous jerking motion that can occur while interfacing weight bearing cartilage surfaces are sliding over each other, and is therefore manifest as decreased resistance both to steady motion and the start-up of motion. Typical wear patterns of cartilage surfaces suggest that boundary lubrication of articular cartilage is critical to the protection and maintenance of the articular surface structure. For example, lubricin null mice show wear but newborn mice, which are not weight bearing, do not. (Jay et al., Arthritis and Rheumatism, 56:3662-3669 (2007).

With increasing loading time and dissipation of hydrostatic pressure, lubricant-coated surfaces bear an increasingly higher portion of the load relative to pressurized fluid, and consequently, $\mu$ can become increasingly dominated by the boundary mode of lubrication. A boundary mode of lubrication is therefore indicated by a friction coefficient during steady sliding being invariant with factors that influence formation of a fluid film, such as relative sliding velocity and axial load. For articular cartilage, it has been concluded that boundary lubrication is certain to occur, although complemented by fluid pressurization and other mechanisms. The lubrication mechanism at the interface of the cornea and eyelid during the eye blink does not involve a significant load, accordingly easing the physicochemical requirements for effective lubrication, and therefore is likely quite different from cartilage lubrication. However, it has been proposed that a boundary mode of lubrication can become dominant when tear film is compromised, such as in dry eye disease.

The two mechanical components of synovial fluid thought to be responsible for its remarkable lubrication properties are lubricin and hyaluronic acid (or hyaluronate or "HA", hereinafter used interchangeably). Lubricin has been shown to function as a boundary lubricant in articulating joints and to protect cartilaginous surfaces against frictional forces, cell adhesion and protein deposition. For example, U.S. Pat. Nos. 6,960,562 and 6,743,774 disclose a lubricating polypeptide comprising substantially pure PRG4 isoforms, and methods of lubricating joints or other tissues by administering systemically or directly to tissues. HA per se has been shown to decrease $\mu$ over saline (0.12 in 3.3 mg/ml HA vs. ~0.24 in PBS) at a cartilage-cartilage interface under boundary mode lubrication, and lubricin alone decrease $\mu$ to still lower levels, but synovial fluid comprising HA in combination with lubricin can impart to interfacing surfaces a coefficient of friction not achieved by lubricin alone or by synthetic mixtures of HA and lubricin. No synthetic composition of lubricin and HA has yet been able to fully duplicate the low coefficient of friction imparted by native form synovial fluid. HA from various sources and various molecular weights have been tested in admixture with lubricins expressed in vitro from synoviocytes, bovine lubricins, lubricins extracted from synovial fluid and "reconstituted" in HA, and lubricins expressed in microgram quantities in early efforts to make it using recombinant DNA technology.

Previous attempts at recombinant production of full length lubricin at a scale suitable for commercial exploitation have not been successful. The very low, single or double-digit milligram per liter rate of production of human lubricin species expressed from CHO cells is considered too low to support a commercial product. One approach to solving this problem was to truncate the number of repeats in exon six, and therefore reduce the mass of glycosylation side chains while retaining at least some lubricating ability (see, e.g., U.S. Pat. Nos. 7,642,236 and 7,893,029). This approach reportedly resulted in a gross productivity (before purification) of the truncated construct of three to four hundred milligrams per liter.

SUMMARY OF THE INVENTION

It has now been discovered that the human PRG4 gene can be used to produce large, commercial quantities of a novel, highly glycosylated human-like form of lubricin, hereinafter referred to simply as "lubricin," multimeric lubricin, rhlubricin, or rhPRG4. This is accomplished as disclosed herein by transfecting the human PRG4 gene (hPRG4) into certain modified Chinese hamster ovary (CHO) cells which have been discovered to be competent to post-translationally glycosylate expressed proteins on a large scale, and then culturing the cells in commercial scale volumes of media, for example, at least 10 liters, more typically at least 50 liters, preferably at least 100 liters or at least 500 liters, and most preferably at 1,000 liters or more.

The lubricin of this invention comprises polydisperse lubricin monomer units forming dimers and multimers and optionally free monomers. Each unit is heavily and variably glycosylated, with the glycosidic residue side chains contributing at least 30%, often 35% or 40%, and possibly as high as 45% or more of its molecular weight.

In native human lubricin, glycosylations consist of core 1 O-linked GalNAc-Gal (N-acetylgalactosamine-galactose) disaccharide, at least 60% of which is terminally substituted with a sialic acid, and also core 2 glycosylation involving addition to core 1 of GlcNac (N-acetylclucosamine) monosaccharides in various isomeric configurations. (See, e.g., Estrella et al., Biochem J., 429(2):359-67 (2010)).

The recombinant material produced as disclosed herein is enriched in core 1 glycans, as compared to native form human lubricin. Its glycosylation comprises at least 95% core 1 side chains, more likely more than 98% or 99%. Furthermore, the side chains often are sulfated to a degree not seen in native human lubricin. This distinguishes the rhPRG4 of this invention from native hPRG4. The increased sulfation content is believed to add additional negative charges to the mucinous glycoprotein which may serve to enhance its ability to repel nearby biomolecules and thus increase its lubricity, and to stiffen the molecular structure, making it more rigid from a molecular standpoint, which can assist in its ability to function in reducing nanoscale and mesoscale friction.

The full length (non-truncated) lubricin monomer sequence (SEQ ID NO:1) comprises 1404 amino acids, or approximately 151 kDa in core protein. The signal sequence of human lubricin is residues 1-24 of SEQ ID NO:1. Accordingly, the mature form of human lubricin is residues 25-1404 of SEQ ID NO:1. Exhaustive reduction of the recombinant product produced as disclosed herein yields a monomeric species with an apparent molecular weight of about 300 kDa-460 kDa, as estimated by comparison to molecular weight standards in a number of molecular weight determination techniques including SDS tris-acetate 3-8% polyacrylamide gel electrophoresis. Glycosylation analysis using mass spectrometry techniques and other work in combination suggested that the true molecular weight of a glycosylated recombinant monomer (as opposed to inferred from gel mobility) likely is in the range of 220-280 kDa, and is unlikely to exceed about 300 kDa. From a total of about 329 possible O-linkages (284 of which are threonines) potentially available as sites of O-linked glycosylation in the sequence of the lubricin monomer, a varying and unknown large number are substituted (100 to 150, perhaps as high as 200 or 220). Of the total glycosylation, about half comprise two sugar units (GalNAc-Gal), and half three sugar units (GalNAc-Gal-Sialic acid). The most abundant form is sulfated Gal-GalNac, the next most abundant is sialylated Gal-GalNac.

The lubricin expression product is resistant, although not immune, to breakdown into monomeric or dimeric lubricin species. The results of exhaustive reduction imply that it comprises disulfide cross-links between and within monomer units. Also, treatment with denaturing buffers without reduction can result in lower molecular weight products, suggesting higher order quaternary structures where the chains also are held together by hydrophobic interaction, hydrogen bonding, physical entanglement and/or other noncovalent associations allowing for self-assembly. The dimers and multimers are polydisperse. Molecular species within it typically have molecular weights of at least about 450-600 kDa, and multimeric species frequently 2,000 kDa or more. Typically, some species of the non-reduced complex essentially do not enter the 3-8% SDS-PAGE gel in an electrophoresis experiment. The larger species of the complex is believed to comprise between three and five, and perhaps as many as 20 monomer units.

Without wishing to be bound by theory, it is believed such larger supramolecular components are formed as a function of monomer/dimer concentration. Currently, a concentration of at least about 0.5 mg/ml monomer/dimer is believed to be optimal for spontaneous formation of larger complex. Concentrations well below this, e.g., less than about 0.1 mg/ml, comprise monomers and dimers, and only a minor amount of complex; concentrations well above can form aggregates visible with the naked eye as a cloudy or hazy solution. Surfactants, preferably physiologically compatible nonionic surfactants that are generally regarded as safe, e.g., polyoxyethylene-based surfactants, or excipients may be used to prevent large aggregate formation while permitting formation of the complex, which appears always to be present together with dimeric species.

Testing of preparations comprising the lubricin of the invention shows that its lubricating and tissue protection properties under load may exceed that of recombinant lubricin heretofore known in the art. Without wishing to be bound by theory, the inventors hereof hypothesize that while stick-slip phenomenon occurs during movement of unlubricated interfacing tissues under load, a coating of the lubricin of the invention can transfer shear away from the underlying cartilage surface to layers within the coating of polydisperse lubricin. That is, the inventors believe that under load and reciprocating motion, the underlying surface experiences less shear, preserving its integrity, as molecules of lubricin within the coating slip over one another, then likely rearrange when the load is removed. (See, e.g., Lee et al., PNAS, 110(7):E567-574 (2013)). The authors state that joint wear is not directly related to the friction coefficient, but more directly related to stick-slip sliding, and that the different molecular components of the joint work synergistically to prevent wear.

In any event, the lubricin product of the invention, when tested, exhibits outstanding lubricating properties, resulting in coefficients of friction (both static and dynamic) often within 150%, 120%, 110% or essentially equal to the coefficients of purified, native bovine lubricin, as measured by cartilage-on-cartilage lubrication testing as disclosed herein. In these tests, the human-like glycoprotein of the invention achieves static coefficients of friction at or below 0.5 and lower than 0.2 (depending on test conditions as disclosed herein), and kinetic coefficients of friction often at or below about 0.1, both as measured by depressurized cartilage upon cartilage bearings in vitro, with a stationary area of contact. When combined with hyaluronic acid (HA), these values improve to below about 0.3 and less than 0.1 for the certain static measurement (depending on dwell time) and less than 0.1 for the kinetic measurement, quite close to the accepted value for synovial fluid. Accordingly, such compositions can dramatically reduce joint wear.

Accordingly, one aspect of the invention comprises a method for the commercial production of lubricin. In one embodiment, the method includes the steps of culturing, in a medium, Chinese hamster ovary (CHO) cells transfected with and which express the human PRG4 gene and post-translationally glycosylate the expression product for a time and under culture conditions sufficient to produce a lubricin glycoprotein, and purifying the lubricin glycoprotein from said medium. For example, in some embodiments, the lubricin glycoprotein is separated from host cell proteins and other contaminants in the extracellular broth to at least partially purify it. The recombinant protein need only be enriched from the culture medium, rather than purified to homogeneity in order to be purified for the purposes of the method of the invention. The method is sufficient to produce a lubricin glycoprotein having at least 30% by weight glycosidic residues at a concentration in the medium of at least 0.4 g/L.

In some embodiments, the CHO cells are CHO-M cells comprising a nucleic acid encoding the human PRG4 gene. In other embodiments the CHO cells are transfected with a first vector comprising a nucleic acid encoding a chromatin element and are transfected with a second vector comprising a nucleic acid encoding the human PRG4 gene. The chromatin element may be a boundary element, a matrix attachment region, a locus control region, or a universal chromatin opening element. In a preferred embodiment, the chromatin element is a matrix attachment region.

In yet another embodiments, the CHO cells are transfected with a first vector comprising a nucleic acid encoding a chromatin element and encoding the human PRG4 gene and are transfected with a second vector comprising a nucleic acid encoding a chromatin elements and encoding the human PRG4 gene. In a preferred embodiment, the chromatin elements in the first and second vectors are matrix attachment region.

In some embodiments, at least 30%, at least 35%, at least 40%, or at least 45% of the weight of the dimeric or multimeric lubricin glycoprotein is the weight of glycosidic residues. In some embodiments, greater than 30%, greater than 35%, greater than 40%, or greater than 45% of the weight of the dimeric or multimeric lubricin glycoprotein is the weight of glycosidic residues. The glycosidic residues may differ from those of native human lubricin as the glycosylation of the recombinant human-like lubricin is at least 90%, at least 95%, or at least 99% by weight core 1 glycosylation. Also, in some embodiments, the glycosidic residues are enriched in sulfated monosaccharides as compared with native human lubricin.

The process, unexpectedly, is capable of producing commercially viable quantities of the full length lubricin glycoprotein. For example, the cells can be cultured for a time and under culture conditions sufficient to produce lubricin glycoprotein concentrations in a culture medium of at least about 0.4 grams or 0.5 grams recombinant lubricin per liter, preferably at least 0.8 grams per liter, and most preferably at least 1.0 grams of lubricin per liter of culture medium in a culture, for example, of at least about 10, 50 or 100 liters. The process when optimized may produce as much as 2.0, at least 2.5, or at least 3.0 grams of lubricin per liter of culture. Depending on development of an optimized purification protocol, it will be possible to obtain at least about 200 milligrams of purified recombinant lubricin per liter, preferably at least 300 mg/L, more preferably at least 500 mg/L, and most preferably more. As far as applicants are aware, these levels of productivity have never before been achieved in recombinant expression of any mucin-like protein, or a protein comparable in size to lubricin, and no previous attempt at expression of PRG4 has succeeded in producing material having the properties of the product described herein.

In preferred embodiments, monomeric lubricin species often are co-purified from the culture medium in admixture with the multimeric protein species. The multimeric species are rich in dimeric lubricin species. For example, in some embodiments, the method produces a mixture of recombinant lubricin that includes monomeric, dimeric, and multimeric lubricin species. In some embodiments, the lubricin glycoprotein comprises at least five disulfide-bonded or non-covalently associated individual glycosylated amino acid chains and has a molecular weight of at least 1200 kDa.

The glycoprotein produced according to the methods of the invention, when tested using the protocol outlined below, produces a coefficient of friction approaching the lowest values ever observed for purified native mammalian lubricin. For example, in some embodiments, the recombinant lubricin glycoprotein is a multimeric protein that produces a static coefficient of friction no greater than 150% of the static coefficient of friction of purified native bovine lubricin as measured in a cartilage on cartilage friction test. In other embodiments, the recombinant lubricin glycoprotein is a multimeric protein that produces a static coefficient of friction no greater than 120% of the static coefficient of friction of purified native bovine lubricin as measured in a cartilage on cartilage friction test. In yet other embodiments, the recombinant lubricin glycoprotein is a multimeric protein that produces a static coefficient of friction no greater than 110% of the static coefficient of friction of purified native bovine lubricin as measured in a cartilage on cartilage friction test.

Another aspect of the invention is directed to compositions of a recombinant, multimeric, lubricin glycoprotein expressed from the human PRG4 gene in a host cell culture. The recombinant lubricin glycoprotein is at least 30% by weight glycosidic residues and produces a dynamic coefficient of friction no greater than 150% of the dynamic coefficient of friction of purified native bovine lubricin as measured in a cartilage on cartilage friction test.

In some embodiments, the recombinant lubricin glycoprotein is at least 35%, at least 40% or at least 45% by weight glycosidic residues.

In some embodiments, the recombinant lubricin glycoprotein produces a dynamic coefficient of friction no greater than 110% or no greater than 120% of the dynamic coefficient of friction of purified native bovine lubricin as measured in a cartilage on cartilage friction test.

In some embodiments, the glycosidic residues of the recombinant lubricin may differ from those of native human lubricin as the glycosylation of the recombinant lubricin is at least 90%, at least 95%, or at least 99% by weight core 1 glycosylation. Also, in some embodiments, the glycosidic residues of the recombinant lubricin are enriched in sulfated monosaccharides as compared with native human lubricin.

In some embodiments, the recombinant lubricin is a mixture of monomeric, dimeric and multimeric species. In some embodiments, the lubricin includes monomeric species. In some embodiments, the lubricin includes dimeric species. In some embodiments, the lubricin includes multimeric species. In some embodiments, the lubricin is a mixture of multimeric and monomeric species.

In some embodiments, the lubricin glycoprotein comprises at least five disulfide-bonded or non-covalently associated individual glycosylated amino acid chains and has a molecular weight of at least 1200 kDa.

In some embodiments, the composition of recombinant lubricin glycoprotein further includes hyaluronic acid or a salt thereof in admixture with the lubricin.

In another embodiment, the invention is directed to a composition comprising a solution comprising 100 grams of human lubricin where the glycosylation of the lubricin is at least 99% by weight core 1 glycosylation. In one embodiment, the lubricin is recombinant human lubricin. In yet another embodiment, the concentration of lubricin in the solution is at least 0.5 g/L. In yet another embodiment, the solution is a cell culture medium.

Compositions of the invention may be used for the preparation of a medicament for any known or hereafter discovered medical or other use of PRG4 glycoprotein, including as a coating for various devices intended for contact with the body (see, e.g., U.S. Patent Application Publication Nos. 2009/0068247 and 2011/0142908); for the treatment of an articular joint in a human or animal by enhancement of joint lubrication (U.S. Patent Application Publication No. 2004/0229804) or viscosupplementation (U.S. Patent Application Publication No. 2008/0287369); for topical application to a tissue surface, e.g., during surgery to inhibit subsequent formation of adhesions or fibrotic connective tissue (U.S. Patent Application Publication No. 2004/0229804); for the treatment of dry eye disease (U.S. Patent Application Publication No. 2011/0059902); for treatment of dry mouth disease (U.S. Patent Application Publication No. 2013/0039865); for treatment of interstitial cystitis (U.S. Patent Application Publication No. 2012/0321693); as a vaginal lubricant (U.S. Patent Application Publication No. 2012/0052077); for a contact lens care and storage solution (U.S. Patent Application Publication No. 2012/0321611) or for systemic injection to, for example, inhibit cell-cell adhesions or motility within the vasculature (see, e.g., U.S. provisional application 61/908,959 filed Nov. 26, 2013).

BRIEF DESCRIPTION OF THE DRAWINGS

FIG. 6 is a diagram showing core 1 glycans of rhlubricin of the invention.

FIG. 7 is a chromatograph, with peaks labeled, showing the relative abundance of the various di- and tri-saccharides pendent from SER and THR residues in the rhlubricin of the invention.

FIG. 8 is a diagram showing the larger range of glycans extending into the core 2 structures on native lubricin extracted from human synovial fluid.

FIG. 9 is a chromatograph, with peaks labeled, showing the relative abundance of the various sugar residues in native human lubricin.

FIGS. 10A, 10B, and 10C are plots of surface tension vs. rhPRG4 and/or polyoxyethylene surfactant concentrations showing the reduction in surface tension with increased concentration of rhPRG4.

FIG. 15 is the amino acid sequence of full length human lubricin which is 1404 amino acids in length. The signal sequence residues (1-24) are shown in bold.

FIG. 16 is the nucleic acid sequence encoding full length human lubricin.

FIG. 17 is a table showing the percentage of each of the glycans identified on the recombinant lubricin. The data includes all isomers, derivatives and adducts for each of the structures listed in the table.

DETAILED DESCRIPTION OF THE INVENTION

Figure 1:
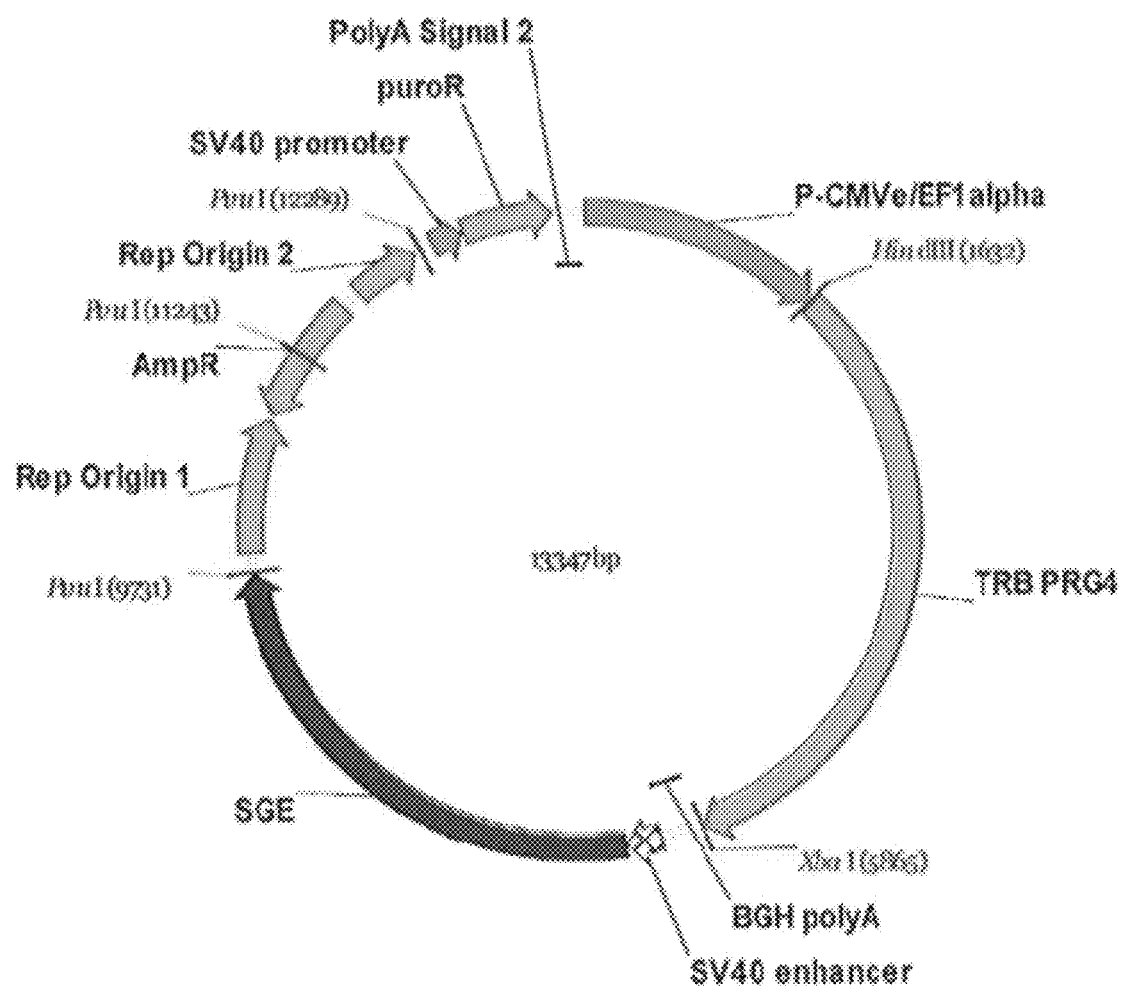
FIGS. 1 and 2 are plasmid maps of vectors used in development of the lubricin-expressing CHO-M clone used in the process of the invention and encoding the full length sequence of hPRG4.

The inventors hereof investigated options for the production of the known human lubricin glycoprotein using recombinant DNA techniques, with the goal of generating a production process involving suspension culture exploiting mammalian cells in serum-free growth medium. Unlike any previous effort known to applicants to produce proteins using recombinant DNA techniques, the challenge was to produce commercial quantities of a complex, large biopolymer who's value lay in its nanoscale mechanical properties, as opposed to its biochemical properties, and those physical properties were dependent on successful exploitation of post translational glycosylation events at a scale never before observed in an engineered cell.

Previous attempts at recombinant production of full length lubricin had yielded only low milligram per liter quantities, and a method of producing at least about one to two grams per liter was needed. A review of the literature revealed no reports of successful recombinant production at commercial scale of full length, properly glycosylated lubricin, nor commercial scale expression of any mucin or mucin-like protein. The search did reveal reports suggesting such a highly glycosylated glycoprotein as lubricin was quite difficult to express. See, e.g., U.S. Pat. No. 7,642,236 which states: "In order to optimize expression parameters and investigate the functional necessity of all approximately 76-78 KEPAPTT (SEQ ID NO:3)-similar sequences, lubricin expression constructs were designed which enabled the synthesis of recombinant lubricin proteins with varying degrees of O-linked oligosaccharide substitution." Productivity data of the recombinant cell lines expressing the truncated lubricin constructs were not disclosed in the patent.

The inventors sought out and ultimately retained Selexis S.A. of Geneva, Switzerland to produce lubricin-expressing clonal cultures, based in part on the reported ability of the Selexis technology, involving expression of epigenetic regulators, to enhance production of difficult to express proteins. (See Selexis U.S. Pat. Nos. 7,129,062 and 8,252,917 and U.S. Patent Application Publication Nos. 2011/0061117, 2012/0231449 and 2013/0143264, the disclosures of which are incorporated herein by reference; Girod et al., Nat Methods 4(9):747-53 (2007); Harraghy et al., Curr Gene Ther. 8(5):353-66 (2008)).

Application of the Selexis technology resulted in development of clones successfully expressing lubricin. After analysis, scale up and purification, it was discovered that the newly developed recombinant production procedures resulted in a never before described, multimeric, heavily and differently glycosylated forms of human-like lubricin, and yields that were at unprecedented levels for such heavily glycosylated, high molecular weight, mucin-like glycoproteins. Testing of preparations rich in the new recombinant lubricin form demonstrated unexpected properties and enabled production of improved physiologically compatible tissue lubricating compositions.

The rhlubricin Manufacturing Process

Host Cells

The Selexis clone production work was done using its proprietary CHO-M cell line, which contains DNA-based elements that control the dynamic organization of chromatin, so-called matrix attachment regions. The CHO-M cell line is a Chinese Hamster Ovary cell line derived from CHO-K1 cells (ATCC, Cat. # CCL-61, Lot. 4765275) adapted to serum free cultivation conditions and used for the production of recombinant proteins. See Girod et al., Nat Methods 4(9):747-53 (2007) and the Selexis U.S. patents and publications identified above relating to matrix attachment regions (MARs) for methods for use of MARs for the development of stable high expressing eukaryotic cell lines such as CHO, and to cells transfected to express proteins involved in translocation of expression products across the ER membrane and/or secretion across the cytoplasmic membrane. CHO-M is used for the production of therapeutic recombinant proteins and allows for higher and more stable expression. Its use permitted isolation of clones exhibiting the desired, high-level expression for use in production of recombinant proteins.

Matrix attachment regions ("MARs") are DNA sequences that bind isolated nuclear scaffolds or nuclear matrices in vitro with high affinity (Hart et al., Curr Opin Genet Dev, 8(5):519-25 (1998). As such, they may define boundaries of independent chromatin domains, such that only the encompassing cis-regulatory elements control the expression of the genes within the domain. MAR sequences have been shown to interact with enhancers to increase local chromatin accessibility (Jenuwein et al., Nature, 385: 269-272 (1997)), and can enhance expression of heterologous genes in cell culture lines. Co-transfection of a plasmid bearing the chicken lysozyme 5' MAR element with one or more expression vectors results in increased stable transgene expression which was shown to produce a 20-fold increase in expression as compared to control construct.

MARs are one type of "chromatin element" (also referred to herein as Selexis Genetic Elements or SGEs) that are disclosed in the Selexis applications and publications referenced herein. Chromatin elements or SGEs are used to prevent the chromatin surrounding the site of integration of a heterologous gene into a host's chromosome from influencing the expression level of the incorporated gene. Chromatin elements include boundary elements or insulator elements (BEs), matrix attachment regions (MARs), locus control regions (LCRs), and universal or ubiquitous chromatin opening elements (UCOEs). SGEs shape the chromatin once the expression vector has integrated in the host cell chromosome and thus maintain the transgene in a highly transcriptionally active state.

The CHO-M host cells were cultivated in SFM4CHO medium (HyClone), supplemented with 8 mM L-Glutamine, hypoxanthine and thymidine (1× HT, Invitrogen). Cells were maintained under agitation (120 rpm, 25 mm stroke) in a humidified incubator at 37° C. and 5% CO2.

Vector Construction

The PRG4 gene encoding the full length 1404 AA human lubricin protein (SEQ ID NO:2) was inserted into plasmid vectors commercially available and proprietary to Selexis S.A. (Geneva, Switzerland) for enhanced gene expression in mammalian cells. Another sequence encoding full length human lubricin is available under GenBank Accession No. NM_005807.3.

Two expression vectors were constructed. The lubricin gene was cloned into expression vectors carrying puromycin resistance and another carrying hygromycin resistance. The vector including the puromycin resistance was designated pSVpuro_C+_EF1alpha(KOZAK-ext9) EGFP_BGH pA>X_S29(2*HindIII, SalI filled) (Mw=9861). The vector including the hygromycin resistance was designated pSVhygro_C+_EF1alpha(KOZAK-ext9) EGFP_BGH pA>X_29 (2*HindIII, SalI filled) (Mw=10299). The expression vectors contained the bacterial beta-lactamase gene from Transposon Tn3 (AmpR), conferring ampicillin resistance, and the bacterial ColE1 origin of replication. As derivatives of pGL3Control (Promega), the terminator region of the expression vectors contained a SV40 enhancer positioned downstream the BGH polyadenylation signal. Each vector also included one human X_29SGE downstream of the expression cassette and an integrated puromycin or hygromycin resistance gene under the control of the SV40 promoter. X_29SGE refers to a Selexis Genetic Element ("SGE"), in this case a matrix attachment region (MAR), that are disclosed in the Selexis applications and publications referenced herein Both expression vectors encoded the gene of interest (PRG4) under the control of the hEF-1-alpha promoter coupled to a CMV enhancer. Plasmids were verified by sequencing.

Figure 2:
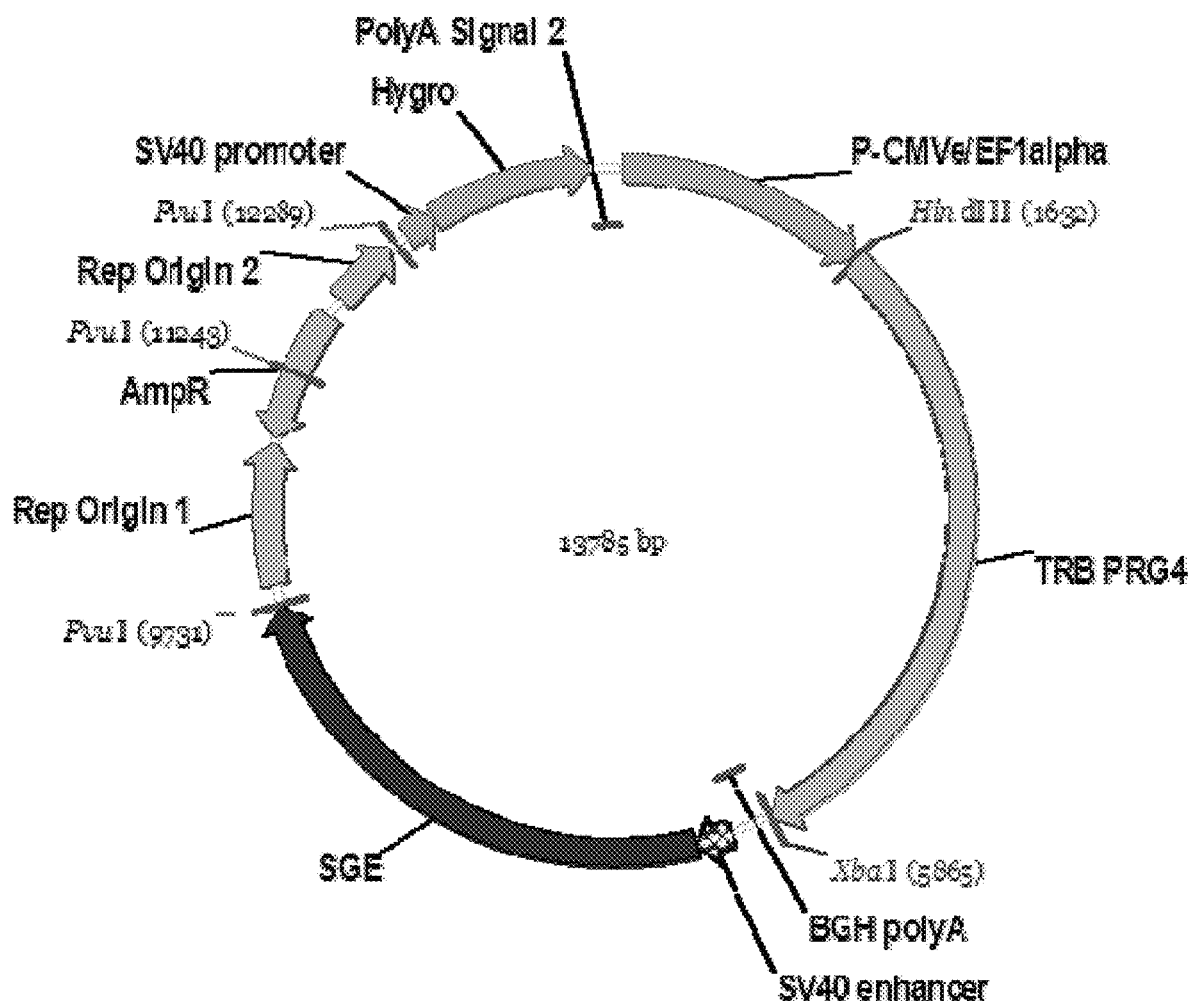

Plasmid maps of the vector carrying the puromycin resistance gene and carrying the hygromycin resistance gene are shown in FIG. 1 and FIG. 2, respectively.

Transfection

The cells were transfected by microporation using a MicroPorator™ (NanoEnTek Inc., Korea) defining the pulse conditions for CHO-M cells (1250V, 20 ms and 3 pulses). Transfection efficiency was controlled using a GFP expressing vector in parallel and showed transfection efficiency between 50-70%. The CHO-M cells were first transfected with the puromycin PRG4 expression vector, and stably transfected cells were selected first by culturing on a medium containing puromycin. More particularly, dilutions were dispensed onto 96-well plates, fed within the following week by adding 100 µL of fresh selection medium to all wells (SFM4CHO medium supplemented with 8 mM L-Glutamine, 1× HT including 5 µg/mL of puromycin). Twenty seven minipools were reset to 24-well plates 15 days after plating by transferring the complete cell suspension out of the corresponding 96-well into one well of a 24-well plate primed with the same medium. Within four days 24-well supernatants were analyzed and 14 minipools were transferred to 6-well plates (1 mL cell suspension+2 mL fresh growth medium incl. selection). Eight best expressing minipools were expanded three days later by suspension and collection in spin tubes (5 mL working volume) and three days later cultivated in shake flasks (20 mL working volume). One subsequent passage was performed before banking.

The pools of resistant cells were expanded in shake flasks to generate material needed for preliminary studies (1-2 mg total). Cell-free media samples were acquired by centrifugation of cell culture at 800 g for 5 min. The expression of recombinant PRG4 was assayed by dot blot analysis. Ten microliters of cell-free media (concentrated sample) was applied on a PVDF membrane (Millipore) and the samples were allowed to spot dry. A PRG4 standard was created by serially diluting PRG4 at 80 µg/ml down to 2.5 µg/ml. Recombinant PRG4 was detected by means of a polyclonal antibody directed against a lubricin synthetic peptide of PRG4 (Pierce).

Cells from the best performing minipools were next super transfected (additional transfection of already selected minipool population), using the second selection marker, the hygromycin resistance cassette. The same transfection protocol was used as described above. One day after this second transfection, selection was started in SFM4CHO medium, again supplemented with 8 mM L-Glutamine and 1× HT, but including 1000 µg/mL of hygromycin. After a media exchange, within four days the three pools were transferred to 6-well plates; all three (3) pools were expanded to spin tubes (5 mL working volume) four days later and to shake flasks (20 mL working volume) within three days.

Clone Generation

The supertransfected pools then were cultivated and analyzed for growth potential in multiple and serial experiments in an attempt to maximize cell properties.

In the first experiment, three super transfected pools (designated P01ST, P05ST and P14ST) were transferred to 6-well plates after the medium exchange at the concentration of 100 cells/mL (2 plates for each pool), in semi-solid medium (2× SFM4CHO medium (HyClone) and CloneMatrix (Genetics), including 8 mM L-Glutamine, 1× HT and Cell Boost 5™ (HyClone), (without selection). Plated cells were screened 16 days later, (ClonePix™ system (Molecular Devices)) and 22 candidates were picked and transferred to 96-well plates with growth medium described above (but without selection). All 18 growing candidates were reset to 24-well plates six days later, by transferring the complete cell suspension out of the corresponding 96-well into one well of a 24-well plate (primed with 1 mL of medium). Within three days 24-well supernatants were analyzed and 12 candidates were transferred to 6-well plates (1 mL cell suspension+2 mL fresh growth medium including selection). The seven best expressing candidates were expanded five days later to suspension cultivation in spin tubes (5 mL working volume) in medium (without selection) and within five days in shake flasks (20 mL working volume).

All cell lines were banked. The performance of the three best candidates was compared in shake flasks (seeding $3\times10^5$ cells/mL, 20 mL culture volume) within fed-batch cultivation (feed strategy—16% of original volume CBS solution (HyClone), 52 mg/mL, fed at day 0, 3, 4, 5, 6, 7). By day 8, the cultures contained $4.22\times10^6$ to $4.95\times10^6$ cells/mL and 94% to 96% viability. Cell populations of these pools were counted and diluted for single cell plating (concentration 1 cell/well, two plates). Single colonies were fed by adding 100 µl growth medium per well after 11 days (without selection). After 17 days, 99 clones were reset to 24-well plates by transferring the complete cell suspension out of the corresponding 96-well into one well of a 24-well plate (primed with 1 mL of medium). Within four days 24 were transferred to 6-well plates (3 mL fresh growth medium incl. selection). Eight clones were expanded to suspension cultivation in spin tubes (5 mL working volume) after four days and all eight clones were expanded to shake flasks (20 mL working volume) after one medium exchange (SFM4CHO medium, supplemented with 8 mM L-Glutamine and 1× HT). One subsequent passage was performed before banking of all candidates.

Comparison of performance of the five best candidates was done in shake flasks (seeding $3\times10^5$ cells/mL, 20 mL culture volume) with fed-batch cultivation (feed strategy A 16% of original volume CBS solution (HyClone), 52 mg/mL, fed at day 0, 3, 4, 5, 6, 7). On day three the cell numbers in the respective cultures ranged from $1.61\times10^6$ to $3.46\times10^6$ cells/mL with doubling times ranging from 19.8 to 30.7 hours. On day 8, the cell concentrations ranged from 4.02×10$^6$ to 9.48×10$^6$ cells/mL with cell viability ranging from 88.6% to 97.7%.

In the second experiment, three different super transfected pools (designated P14STcp08, P05ST11 and P14ST33) were treated to the same procedure as outlined above. This resulted in four clonal cell lines. Again, the performance of these clones was compared in shake flasks, resulting in day 8 cell concentrations ranging from 3.5×10$^6$ to 9.48×10$^6$ cells/mL and viability between 75.3% and 88.1%.

A clone from the first round of ClonePix™ system selection described above (P14ST15) which exhibited on day eight 6.03×10$^6$ cells/mL and 95.5% viability was thawed in a shake flask (20 mL working volume). The candidate was transferred to a single plate after one subsequent passage, at the concentration of 200 cells/mL (1 plate) in the semi-solid medium described above plus CloneMatrix, including 8 mM L-Glutamine, 1× HT and Cell Boost 5™ without selection. Plated cells were screened using the ClonePix™ system 12 days later, 84 clones were picked and transferred to 96-well plates (without selection). Single colonies were fed by adding 100 µl growth medium per well. Screening of 96-well supernatants took place 18 days after plating. The best 24 growing clones were reset to 24-well plates, by transferring the complete cell suspension out of the corresponding 96-well into one well of a 24-well plate (primed with 1 mL medium (without selection). Within three days 24-well supernatants were analyzed and 12 clones were transferred to 6-well plates (1 mL cell suspension+2 mL fresh growth medium including selection). The six best expressing clones were expanded four days later to suspension cultivation in spin tubes (5 mL working volume) and within four days in shake flasks (20 mL working volume). Two subsequent passages were performed before banking. Six clonal cell lines were banked.

The performance of six best candidates was compared in shake flasks as described above. On day 8 cell densities ranged between 9.04×10$^6$ and 6.40×10$^6$ cells/mL and viabilities were between 74.6% and 93.1%.

Cryoconservation and Testing

After multiple passages of the clonal pools (from 6 to 31), the pools were cryopreserved in vials at 6×10$^6$ cells/vial and stored in liquid nitrogen. Absence of mycoplasma for all cell lines was confirmed by using Venor® Gem mycoplasma detection kit (Minerva Biolabs). Sterility tests were inoculated and incubated according to the manufacturers protocol (Heipha, Caso-Bouillon TSB). Sterility for all minipools and supertransfected minipools were confirmed.

Scaled-Up Cultures

The cell line designated P05ST11-cp05 was selected for scale up. For a 200 liter run, the following conditions and protocol were used:

| | |
|---|---|
| Vessel | XDR-200 Bioreactor |
| pH | 7.1 ± 0.2 |
| Dissolved Oxygen | 50% |
| Temperature | 37° C., see shift notes below |
| Starting Volume | 100 L |
| Inoculum Density | 1e6 VC/mL |
| Base Medium | SFM4CHO Supplemented w/ 1XHT + (8 mM) Glutamax (Gibco ®) |
| Feed | CellBoost5 (52 g/L) 16% v:v on days 0, 3, 5, 7 |
| | *CellBoost5 (52 g/L) 10% v:v days 10 and 12, further if needed. |
| Target culture glucose | Maintain 4-4.5 g/L |
| | Feed with 40% stock as required, see "Glucose/Osmolarity" below |
| WFI Supplementation | As required to maintain Osm ≤ 410 mOsm/kg, see "Glucose/Osmolarity" below |
| Harvest Criteria Cell Viability | 60% viability |
| Agitation | 95 RPM |
| Gas Sparge Design | (5) 0.5 mm drilled holes in 2um porosity disc |
| Cell Boost ™ Feed | 16% of 52 g/L on days 0, 3, 5, 7 |
| | 10% of 52 g/L on day 10, 12, and further if needed |
| Glucose/Osmolarity | measurement protocol: Feed - Measure Glucose - Add Glucose as Necessary - Measure Osmolarity - Add Water as Necessary |
| | Glucose Criteria: 4-4.5 g/L |
| | Osmolarity Criteria: If >410 mOsm, add H$_2$0 to target 390 |
| Glutamax/Glutamine | Monitor Glutamine - if drops to <0.5 mM, supplement to 2 mM |
| Temperature Shift | Shift to 34 C. at 80% or 12 × 10$^6$ cells/ml |
| Harvest Criteria | Viability < 60% |

Figure 5:
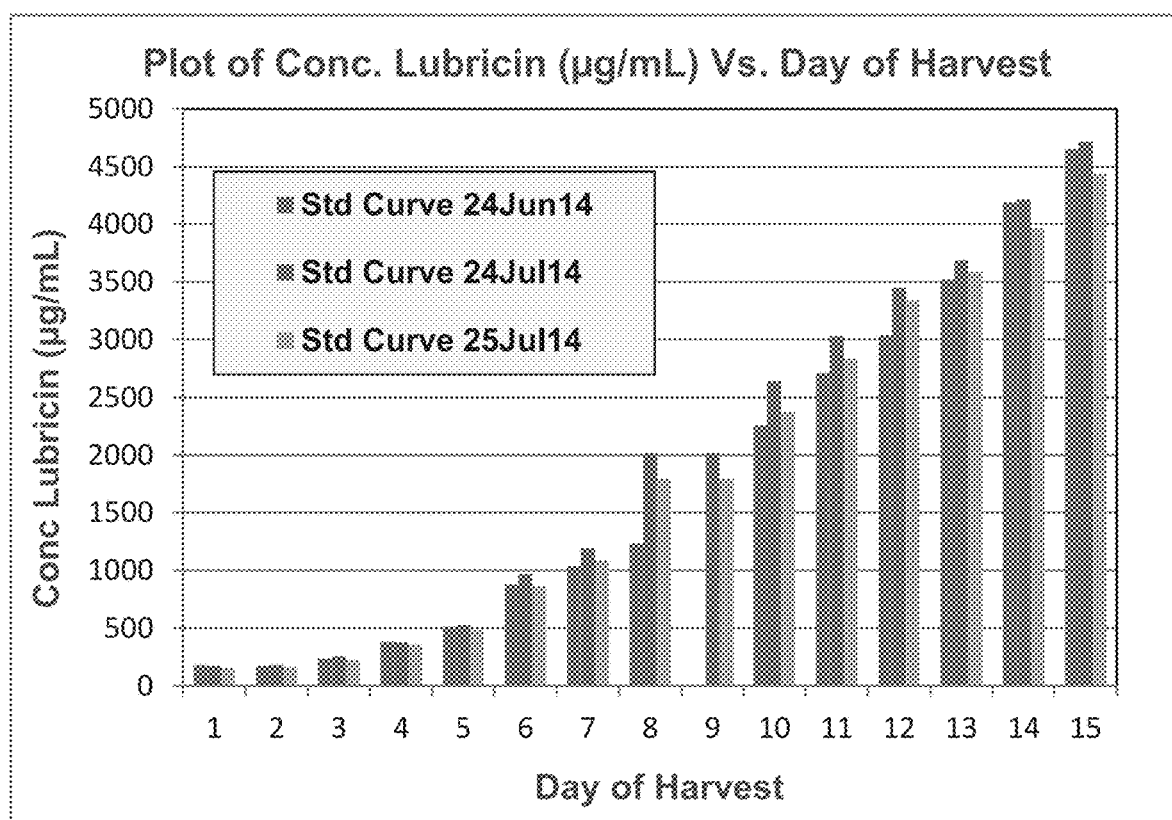
FIG. 5 is a graphical depiction of the productivity of one lubricin production run measuring micrograms of lubricin produced over time per liter of culture of transfected CHO-M cells. There are three bars at each date of harvest. The bar at the left is "Std Curve 24 June 14." The bar in the middle is "Std Curve 24 July 14," and the bar at the right is "Std Curve 25 July 14."

The expression of rhPRG4 increases in tandem with the viable cell density (VCD) from day 1 to 8 in a 200 liter culture. The VCD plateaus by day 8 then begins to fall, which is typically seen once conditions are no longer optimal for the metabolic demands of a dense cell culture system. In spite of this, the expression of rhPRG4 continues unabated and its expression in the culture system with VCD of 12-14×10$^6$ cell/ml reached a maximal concentration on culture day 13. FIG. 5 shows the cumulative amount of recombinant lubricin over time as measured using the area under the curve of an HPLC plot, and interpreting this area by comparison with three different standard curves made by HPLC purification of serially diluted samples of what is believed to be at least 99% pure lubricin. As illustrated, this procedure estimated recombinant lubricin production near 2.5 g/ml. Additional production runs varied in their apparent yield as measured by various techniques. One run produced lubricin at a 1.5 g/liter level as measured by competitive ELISA. Another produced a reading of 1.4 g/liter.

Purification of Recombinant PRG4

The goal of development of the purification protocol is to retain the lubricating function of the expressed lubricin product and its multimeric complexes while separating it from contaminants, avoiding aggregation, and maintaining a high yield. This was a challenge because of the heavy glycosylation of lubricin, its high molecular weight, its property of anti-adhesion and surface lubrication, and its tendency to form complexes, and to aggregate to form insoluble microparticles as purity increases. Early experiments suggested that because the lubricin titer in the harvested media was high, flow through mode chromatography might be necessary to avoid purification losses. A strategy was developed to extract contaminants by chromatographic adsorption while retaining lubricin product in the flow through. During the course of development it was discovered that yield was sensitive to the use of nonionic surfactant components such as, for example, polyoxyethylene derivative of sorbitan monolaurate. Omission of such a surfactant in the lubricin pool resulted in significant loss of product during the ultrafiltration/diafiltration and 0.2 μm filtration after the chromatographic separation steps. Use of as little as 0.1% by weight surfactant greatly improved yield. By trial and error it was discovered that lower concentrations of surfactant succeeded in retaining function and improving yield.

In addition to nonionic surfactants used in the purification process, physiologically compatible forms of excipients, such as [(3-cholamidopropyl) dimethylammonio]-1-propanesulfonate (CHAPS) and/or lysine may be mixed with solutions of the lubricin of the invention and can have beneficial effects in stabilizing solutions, e.g., to avoid or reduce aggregation of lubricin in solutions containing greater than a concentration of 0.4 or 0.6 mg/ml.

Iterative testing resulted in development of a purification procedure set forth below.

Media clarified by sedimentation (100 mL) was diluted with 5 mL 200 mM Tris, 40 mM MgCl2, pH 8.2 and mixed with 400 units of Benzonase (250 units/μl, Novagen) to remove soluble polynucleotides. The solution was mixed for four hours at room temperature, then mixed with 37.8 g urea to adjust urea concentration to 6M, and to result in 120 mL of solution. To this was added 1N NaOH to adjust to pH 11 and 0.01% Tween 20 (sorbitan monolaurate, Sigma).

The post-Benzonase material was next treated using GE Q Big Beads™ anion exchange resin with pH of 11 in the presence of 6M Urea and 0.01% Tween 20 run in flow through (FT) mode where the contaminants bind to the resin and the product does not. The column was first sanitized with 0.1N NaOH; then charged with 100 mM NaPO4, 1.5M NaCl, pH 7.2; and re-equilibrated with 200 mM Tris-Borate, 6M Urea, pH 10. The 30 ml volume (XK 26×6 cm) column was then loaded with the 120 ml solution at 4 ml/ml resin at a flow rate of 20 ml/min (240 cm/hr), followed by a wash with equilibration buffer—100 mM Tris-Borate, 100 mM NaCl, 6M Urea, 0.01% Tween 20, pH 11. Shortly after loading, product was collected through the wash (290 mL total volume) until addition of a strip solution 0.1N NaOH+ 1M NaCl.

This partly purified flow-through lubricin pool was pH adjusted with 1M Citrate pH=7.5, and passed through a hydroxyapatite column (BioRad CHT), Column Volume—14 ml (XK 16×7 cm), Column Load—21 ml Load/ml resin, Flow rate=10 ml/min (300 cm/hr). The column was first sanitized with 0.1N NaOH and 1 M NaCl, Charge with 500 mM NaPO4, pH 6.5; re-equilibration with 500 mM NaPO4/ 6M Urea, pH 7.4; and loaded with the 290 mL flow through from the step above. This was followed by wash with equilibration buffer, 15 mM NaPO4, 6M Urea, 0.01% Tween 20, pH 7.4, to produce 305 ml of flow-through containing the product.

The flow through from the hydroxyapatite column was adjusted to pH 4.8 with 1M citrate and diluted with water, then passed through a GE SP Big Bead resin, Column Volume—6 ml (XK 1.6×3 cm), Column Load—58 ml Load/ml resin, Flow rate=6.7 ml/min (200 cm/hr). The column was first sanitized with 0.5N NaOH, charge with 100 mM NaPO4, 1.5M NaCl, pH 7.4; re-equilibration with 50 mM Na citrate/6M urea, 0.01% Tween 20, pH 4.8; and loaded with the 350 mL flow through from the step above. This was followed by wash with equilibration buffer, 50 mM Na citrate/6M Urea, 0.01% Tween 20, pH 4.8, to produce 378 ml of flow-through containing the product. The flow-through was then neutralized with 10N NaOH (pH 7.2).

To concentrate and buffer exchange, the post cationic exchange flow-through product pool was filtered using a 50 kDa molecular weight cut-off TangenX 0.01 m$^2$ flat sheet membrane (TangenX Technology Corporation), LP screen channel. The diafiltration buffer was 10 mM NaPO4, 150 mM NaCl, pH 7.2 (PBS) and 0.1% Tween 20. After sanitization with 0.1N NaOH; a rinsed with MilliQ water; and equilibration with 10 mM NaPO4, 150 mM NaCl, pH 7.2, the membrane was loaded at 15,000 ml/m$^2$; Cross-flow 70 ml/min; transmembrane pressure=6-7 psi; permeate flow=5-6 ml/min to concentrate the solution to approximately 50 ml.

Lastly, the post UFDF product pool was subject to 0.2 μm filtration through a Sartorius Sartopore 2, 150-0.015 m$^2$ membrane at a membrane load of ~17,000 ml/m$^2$, and a flow rate of 45-50 ml/min. The membrane was first primed with 10 mM NaPO4, 150 mM NaCl, pH 7.4, then the product was filtered, followed by a chase filter with ~40 ml of buffer and finally the filter was drained.

Additional excipients are currently being examined to improve recovery from the UFDF and 0.2 um filtration of the final purified product. This procedure can yield large amounts of product per liter of harvested media of at least 96% purity. Alternative purification strategies will be apparent to those of skill in the art.

Characterization of Lubricin Product

Electrophoresis

The molecular weight of the full length lubricin amino acid backbone is 150,918 Daltons. The extent and type of glycosylation varies from molecule to molecule. The recombinant PRG4 made as disclosed herein as a dimeric species is believed to have an average molecular weight of greater than about 450 kDa. Monomers should have a weight of 220-280 kDa, and no greater than about 300 kDa.

Figure 3:
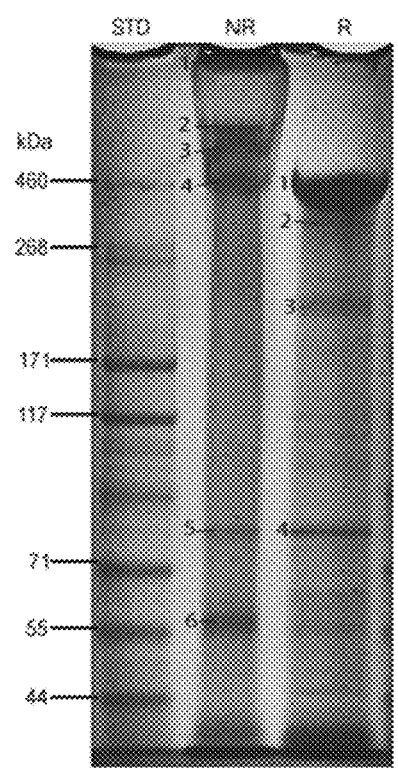
FIGS. 3 and 4 depict polyacrylamide gels useful in assessing the structure of the rhlubricin of the invention.

FIG. 3 depicts a Coomassie Stained gel (Tris-Ac 3-8% NuPAGE® SDS-PAGE polyacrylamide gel electrophoresis system, Invitrogen) of rhPRG4, both non-reduced as purified and reduced and alkylated. All numbered bands were confirmed as lubricin by MS/MS, having amino acid sequence matching homo sapien PRG4 (UniProt Accession No. Q92954; SEQ ID NO:1). As illustrated, recombinant lubricin produced as described above (NR) contains a major bands having approximate molecular weights, as estimated by comparison to molecular weight standards, of ~460 kDa, one slightly above it, and one at the top of the gel that was unable to migrate into the gel.

Figure 4:
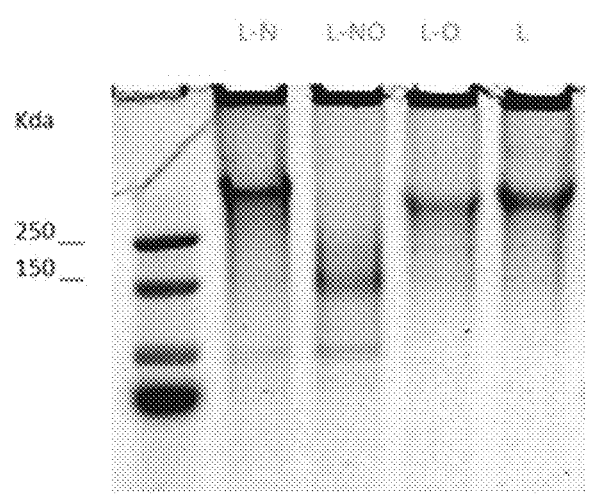

Identification of post-translational processing constituents was done by digestion of rhPRG4 with neuraminidase (NaNase 1) and O-glycosidase DS simultaneously to expose the molecular weight of the amino acid core of rhPRG4 as shown in the lane labeled L-NO in FIG. 4. The predicted molecular weight of the core is 151 kDa which is experimentally confirmed by this 4-12% SDS-PAGE. Digestion with neuraminidase alone had a lowering effect on molecular weight illustrating that the glycosylation is incompletely capped by neuraminic acid. Digestion with O-glycosidase DS which removes O-linked β(1-3) GalNAc-Gal residues and neuraminidase implies that this batch of protein is roughly 30% by weight glycosylated. Digestion with O-glycanase alone is likely only effective in removing some uncapped GalNAC-Gal residues.

Glycosylation Analysis

To further characterize the protein, mass spectrometric analysis of the O-glycans from recombinant lubricin and normal synovial lubricin was conducted and compared. Briefly, synovial lubricin was isolated from synovial fluid using DEAE chromatography. Recombinant and synovial lubricin were separated by SDS-PAGE using 3-8% Tris-acetate gels before transferring to PVDF membrane. O-glycans were then released from the lubricin blots by reductive β-elimination followed by clean-up for LC-MS/MS analysis. O-glycans were separated by porous graphitized carbon chromatography before MS/MS analysis in negative mode using a data-dependent method on a linear ion trap mass spectrometer, LTQ (Thermo Scientific).

Analysis of the recombinant lubricin sample identified only core 1 O-glycan structures (FIG. 6). The extracted ion chromatograph displaying the identified glycans is shown in FIG. 7. The sialylated structure, [M-H]– 675, is shown as two major peaks. These are the same isomer with the second peak at retention time 21.4 min being a chemical derivative created during the β-elimination process. Three isomers of the sulfated structure ([M-H]– 464) were identified. Several isomers of the monosulfated monosialylated structure also were identified. The disialylated structure was of very low abundance and cannot be observed in the chromatograph. An estimation of the proportion of each of the glycans identified is shown in FIG. 17. (For key to sugar structures, see FIG. 6). This analysis combines all isomers, derivatives and adducts for each of the structures in FIG. 17.

Normal human synovial lubricin has a larger range of glycans extending into the core 2 structures (FIG. 8). The most abundant of these structures are shown in FIG. 9 on the extracted ion chromatograph.

The glycosylation pattern of the rhlubricin is very different from the native human glycoprotein, as can be readily appreciated, for example, from a comparison of FIG. 7 with FIG. 9. On native synovial lubricin, the sialylated core 1 structure is the most abundant glycan, but there is significant core 2 glycosylation of various kinds, and only minor amounts of sulfated polysaccharides. On the recombinant glycoprotein, sialylated and unmodified core 1 makes up over half of the glycans, and the sulfated core 1 structure makes up about one third of the identified O-glycans, with all three possible isomers identified.

Physicochemical Properties of rhlubricin

Surfactant-Like (Amphipathic) Properties

An important attribute of rhPRG4 is its ability to coat both biological and non-biological surfaces via physicochemical adsorption. Native PRG4 is surface active, and incorporates terminal globular domains separated by the large mucin-like domain. These can separate into polar and non-polar domains within its structure. The central mucin domain, as shown by surface force apparatus studies of human synovial fluid lubricin, can fold back upon itself suggesting that the glycosylations are directed away as this orientation is achieved. Overall, the mucin domain becomes more hydrophilic than either its N- or C-termini. The importance of this is confirmed by the knowledge that digestion of the glycosylations will remove lubricating ability (Jay et al., J Glycobiol 2001). This amphipathic nature also is present in rhPRG4. It can be measured readily by assessment of a reduction in interfacial tension between an aliphatic and aqueous interface.

In an experiment designed to test the surfactant properties of rhlubricin made using the process of the invention, an increasing concentration of rhPRG4 was presented in a solution of PBS which was covered by undiluted, hydrophobic cyclohexane. A Du Noüy ring placed in the aqueous sub-phase containing rhPRG4 was pulled upward and the critical tension ($\tilde{\Gamma}_i$) where the ring breaks through the interface was recorded. Measurements were collected five times at each concentration in an Attension Sigma 702ET tensiometer. A dose response curve of concentration of rhPRG4 was plotted against $\tilde{\Gamma}i$, see FIG. 10A. As illustrated, as the concentration of rhPRG4 increases in the aqueous sub-phase containing PBS, interfacial tension decreases.

Figure 10B:
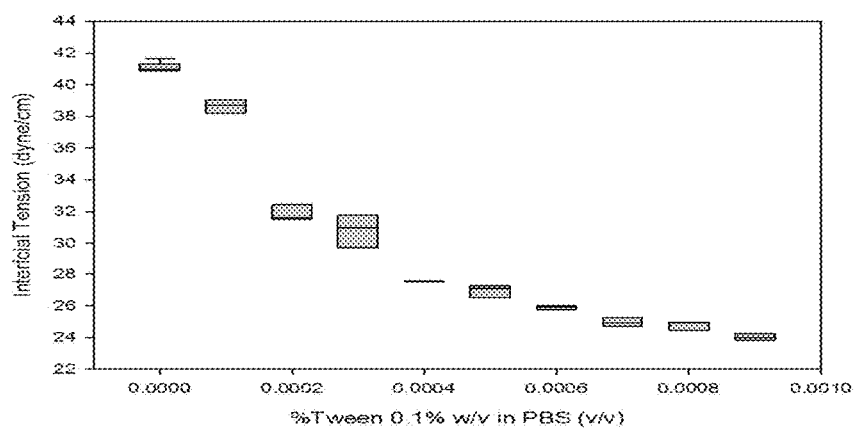
Figure 10C:
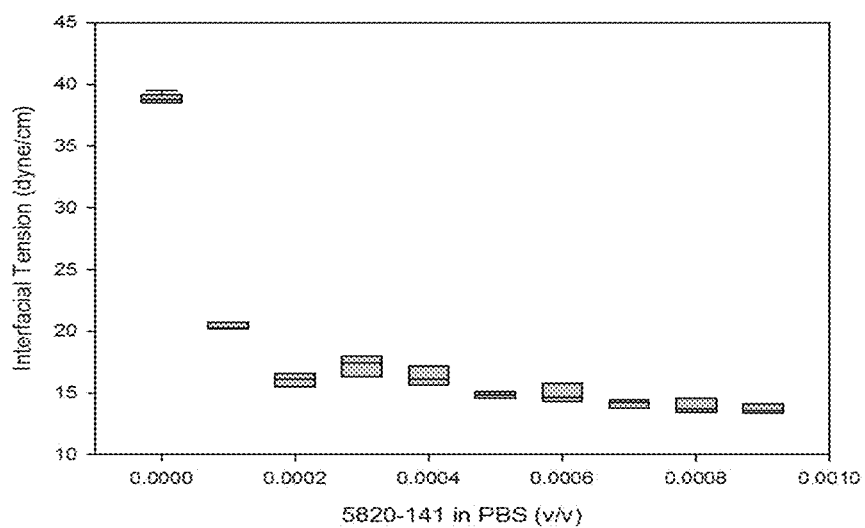

Because the rhlubricin solution contained residual non-ionic surfactant (Tween 20), the experiment was repeated to investigate whether this was responsible for the dramatic reduction in surface tension induced by addition of the recombinant product, first using various concentrations of the surfactant alone, and then with very low concentrations of the rhPRG4 of the invention. Microliter quantities of the surfactant and PRG4 were added to 15 mL of the aqueous sub-phase. The results are shown in FIG. 10B and FIG. 10C. As illustrated, PRG4 alone (FIG. 10C) reduces surface tension better than the commercial surfactant alone at 0.1% (FIG. 10B). Thus, rhPRG4 containing 0.1% Tween and not containing Tween reduced interfacial tension of PBS and cyclohexane more than 0.1% Tween alone when all had the same amounts of the solution of interest added.

These data show that even at low concentrations, rhPRG4 preferentially populates the aqueous-aliphatic interface, reducing interfacial tension. This phenomenon recapitulates the surface binding interaction which is required in the reduction of friction and mimics the behavior of native lubricin. Furthermore, the activity of interfacial tension reduction can be used as a quality control procedures of rhPRG4 production.

Lubricating Properties

Cartilage Lubrication

Fresh osteochondral samples (n=16) were prepared for friction testing from the patella-femoral groove of skeletally mature bovine stifle joints, as described previously. Briefly, cores (radius=6 mm) and annuluses (outside radius=3.2 mm and inside radius=1.5 mm) were harvested from osteochondral blocks, both with central holes (radius=0.5 mm) to enable fluid depressurization. Samples were rinsed vigorously overnight in PBS at 4° C. to rid the articular surface of residual synovial fluid, and this was confirmed by testing for the presence of lubrication. Samples then were frozen in PBS with proteinase inhibitors at –80° C., thawed, and re-shaken overnight in PBS to further deplete the surface of any residual PRG4 at the surface. Samples were then completely immersed in about 0.3 ml of the respective test lubricants (described below) at 4° C. overnight prior to the next day's lubrication test, and were again rinsed with PBS after each test before incubation in the next test lubricant.

A Bose Electroforce test instrument (ELF 3200, Eden Prairie, Minn.) was used to analyze the boundary lubrication ability of each of the PRG4 forms and controls, using an established cartilage-on-cartilage friction test. Briefly, all samples were compressed at a constant rate of 0.002 mm/s to 18% of the total cartilage thickness, and were allowed to stress-relax for 40 minutes to enable depressurization of the interstitial fluid. The samples then were rotated at an effective velocity known to maintain boundary mode lubrication at a depressurized cartilage-cartilage interface (0.3 mm/s) at ±2 revolutions. After being left in a pre-sliding stationary period of 1200, 120, 12 and 1.2 seconds, samples were rotated after each subsequent stationary period, +/–2 revolutions. The test sequence was then repeated in the opposite direction of rotation, −/+2 revolutions.

Two test sequences assessed the cartilage boundary lubricating ability of rhPRG4, both alone and in combination with HA. In both test sequences, PBS served as the negative control lubricant and bovine synovial fluid as a positive control lubricant. Both rhPRG4 and purified native bovine PRG4 were prepared in PBS at a concentration of 450 µg/mL, and HA (1.5 MDA Lifecore Biomedical, Chaska, Minn.) was also prepared in PBS at a physiological concentration of 3.33 mg/mL. Lubricants were tested in presumed increasing order of lubricating ability (decreasing coefficient of friction). In test sequence 1, rhPRG4 vs. nbPRG4, the sequence was PBS, rhPRG4, nbPRG4, synovial fluid (n=7); in test sequence 2, rhPRG4 vs. rhPRG4+HA, the sequence was PBS, rhPRG4, rhPRG4+HA, synovial fluid (n=4).

Figure 11A:
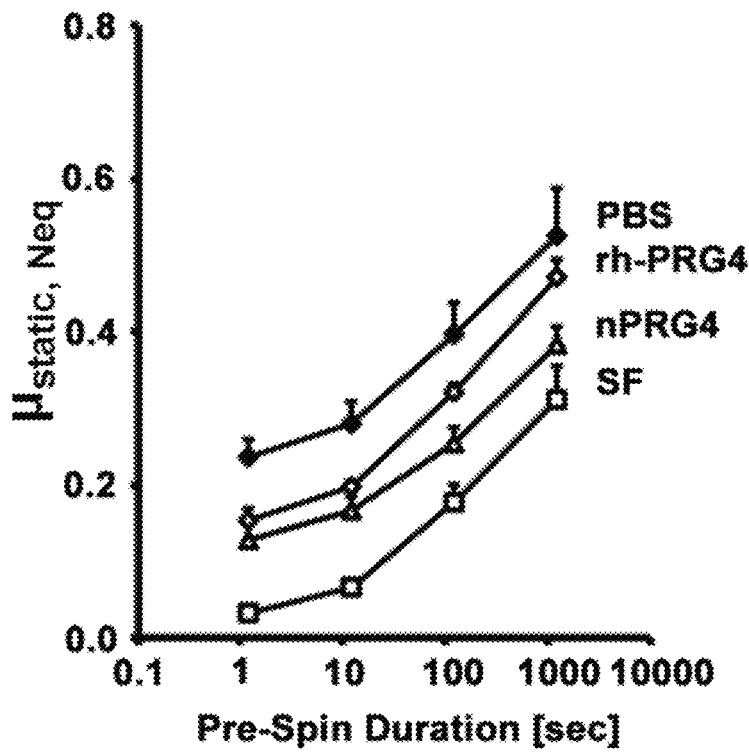
FIGS. 11A and 11B depict data comparing the static (FIG. 11A) and kinetic (FIG. 11B) friction coefficients of rhPRG4 solution to purified native bovine PRG4, saline (PBS), and bovine synovial fluid, with both PRG4 preparations 450 µg/mL. The designations a, b, and c signify statistically significant differences in the results (p<0.05). n=7. There was no statistically significant difference in the results for rh-PRG4 (recombinant) and nPRG4 (native) as indicated by the presence of "b" above each bar in FIG. 11B.
Figure 11B:
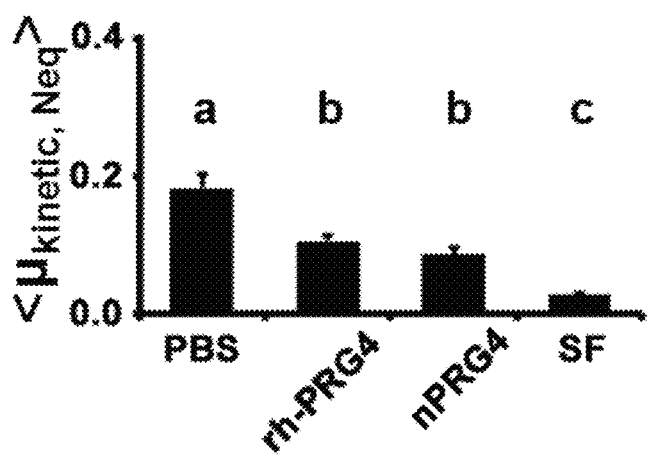

The two coefficients of friction; static ($\mu_{static}$, $N_{eq}$) (resistance of start-up motion from static condition) and kinetic ($<\mu_{kintic}$, $N_{eq}>$) (resistance of steady sliding motion) were calculated for each lubricant as described previously. The results are shown in FIGS. 11 and 12. Data is presented as mean±SEM. ANOVA was used to assess the effect of lubricant and pre-sliding stationary period as a repeated factor on $\mu_{static}$, $N_{eq}$ and $<\mu_{kinetic}$, $N_{eq}>$, with Tukey post hoc testing on $<\mu_{kinetic}$, $N_{eq}>$ at a pre-sliding stationary period of 1.2 s. Statistical analysis was implemented with Systat12 (Systat Software, Inc., Richmond, Calif.).

Figure 12A:
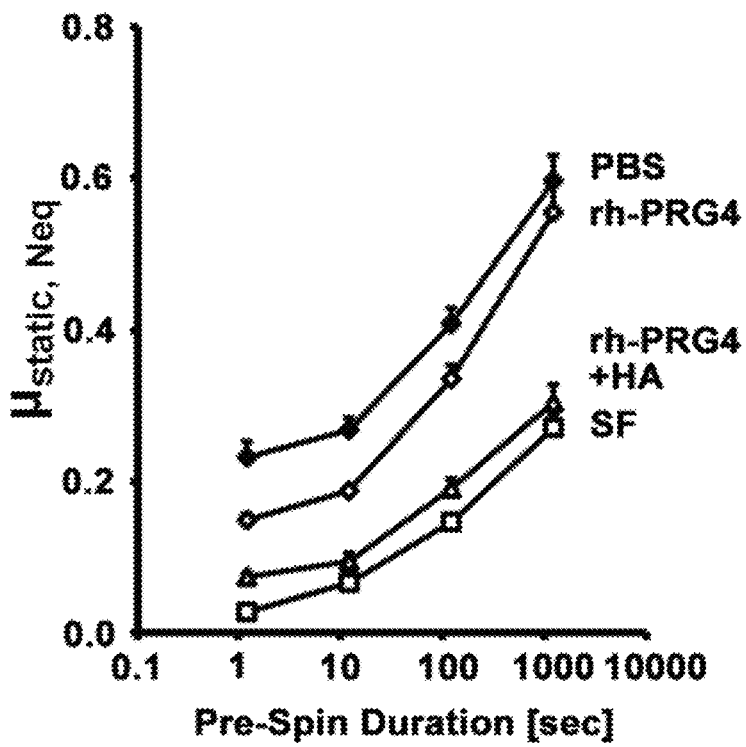
FIGS. 12A-B depict data comparing the static (FIG. 12A) and kinetic (FIG. 12B) friction coefficients of an HA plus rhPRG4 solution to saline, rhPRG4 alone, and bovine synovial fluid with rhPRG4 at 450 µg/mL and HA (1.5 MDa) 3.33 mg/mL. The designations a, b, c, and d above each bar in FIG. 12B signify statistically significant differences in the results (p<0.05), n=4.
Figure 12B:
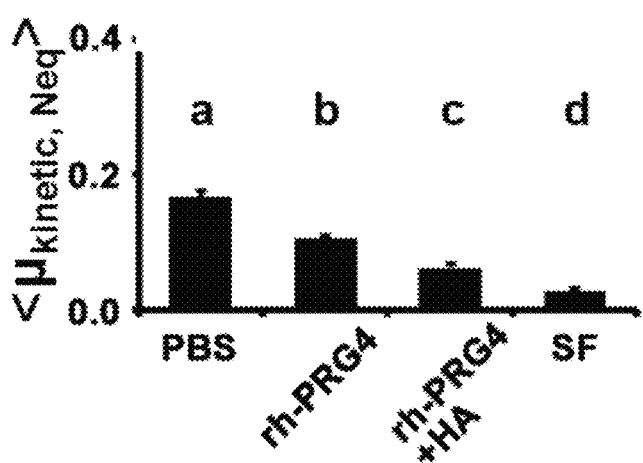

As shown in FIG. 11, there was no statistical significance between the measured lubricating property, kinetic coefficients of friction, of recombinant PRG4 and the slightly lower values of native bovine PRG4. As shown in FIG. 12, rhPRG4 in combination with HA improves both static (FIG. 12A) and kinetic (FIG. 12B) lubricity as compared with rhPRG4 alone. All measurements were highest in PBS and lowest in bovine synovial fluid, with rh-PRG4 and rhPRG4+HA being intermediate. The mixed solution of rhPRG4+HA had a trend toward significantly lower coefficient of friction than rhPRG4 alone (p=0.075) and was statistically similar to bovine synovial fluid (0.021±0.001, p=0.20).

Figure 13:
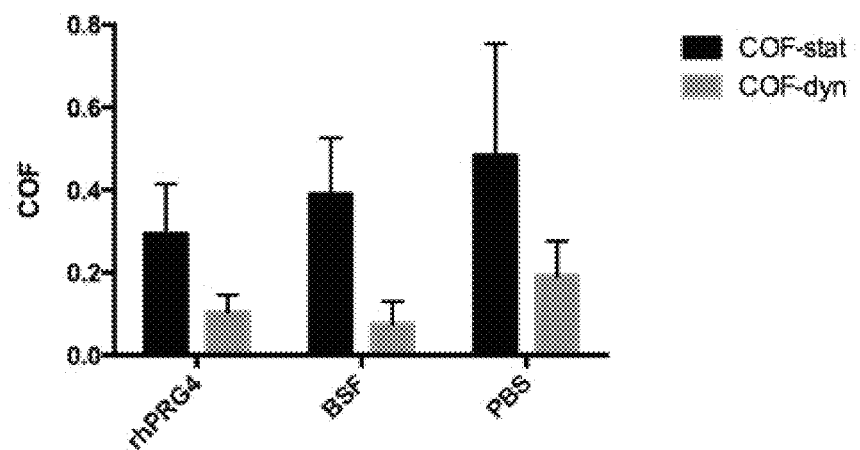
FIG. 13 depicts data showing reestablishment of lubricity at interfacing bovine tissue surfaces after digestion of native bovine PRG4 and application of rhPRG4.

Efforts also have been made to assure removal of native lubricin from bovine cartilage intended to be used as bearings using a two-hour enzymatic digestion with hyaluronidase. Hyaluronidase digestion is intended to remove native PRG4 (P<0.050) from the superficial zone of the cartilage explants. This treatment removes surface PRG4 without significantly affecting the mechanical characteristics of the articular cartilage. Applying rhPRG4 to these surfaces and comparing the frictional response to BSF and PBS controls shows that a low COF can be re-established with the rhPRG4 of the invention. FIG. 13 shows COF values for hyaluronidase-treated bovine medial condyle cartilage explants with rhPRG4, BSF and PBS as intervening lubricants. Osteochondral explants were tested following the aforementioned lubricants following the protocol discussed above. As shown, recombinant human like PRG4 re-established a low COF (rhPRG4 N=18; BSF N=6; PBS (N=8).

Ocular Surface Lubrication

Normal human corneas with 3 mm of sclera were obtained from the Southern Alberta Lions Eye Bank. Human eyelids were harvested from fresh cadavers from the University of Calgary body donation program. Approval for use and appropriation of these tissues was obtained from a Health Research Ethics Board. The corneas (n=6) were stored in chondroitin sulfate-based corneal storage media (Optisol-GS) at 4° C. and used within 2 weeks. The eyelids (n=6) were frozen and thawed at time of use.

The purity of the rhPRG4 species was assessed to be 50% by 3-8% Tris-Acetate NUPAGE sodium dodecyl sulfate polyacrylamide gel electrophoresis. The concentration of the enriched rhPRG4 preparation was assayed and adjusted to take the level of purity into account.

Tissue samples were mounted on a Bose ELF3200 with axial and rotational actuators, and axial load and torque sensors. The resected cornea was fixed to the end of a semi-spherical silicone rubber plug (radius=6 mm) by applying cyanoacrylate adhesive (superglue) to the sclera. A silicone rubber sleeve was fitted around the cornea-plug apparatus, which served to hold lubricant fluid. This apparatus was then attached to the rotational actuator of the Bose ELF3200 thus forming the bottom articulating surface. An annulus (outer radius=3.2 mm, inner radius=1.5 mm) was punched from the model PDMS material (~0.4 mm thick UntrSylgard 184, Dow Corning,) or human eyelid tissue and glued to an annulus holder. This annulus holder was then attached to the linear actuator, thus forming the upper articulating surface.

After mounting the samples, 0.3 ml of test lubricant was placed on the cornea to form a lubricant bath and the articulating surfaces were allowed to equilibrate with the test lubricant for a minimum of five minutes. The tissue samples are brought into contact at three manually determined axial positions to correspond with axial loads of 0.3±0.02, 0.5±0.03, and 0.7±0.03 N, resulting in axial pressures ranging from 12.2 to 28.5 kPa based on a contact area of (24.6 mm$^2$). Once in contact at a given axial position, the samples underwent four revolutions in both directions at four different effective sliding velocities ($v_{eff}$=30, 10, 1.0, 0.3 mm/s) where $v_{eff}=\omega \cdot r_{eff}$ and $r_{eff}=\frac{2}{3}[(r_o3-r_i3)/(r_o2-r_i2)]$. Axial load and torque were collected at 20 Hz during rotations. There was a 12 second dwell time between each revolution. Each test sequence, described below, included a preconditioning step where the tissues underwent the described test protocol in a saline bath.

To determine the boundary lubricating ability of the rhPRG4 preparation at a human cornea-eyelid (Test 1) and human cornea—Polydimethylsiloxane (PDMS, Test 2) interface, the following test sequence was used: 300 µg/mL PRG4 in saline, 300 µg/mL rhPRG4 in saline, then saline (Sensitive Eyes Saline Plus, Bausch & Lomb).

Figure 14A:
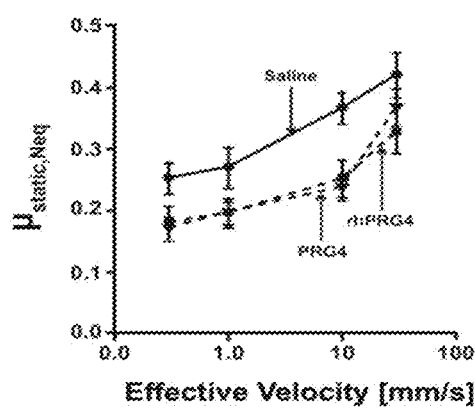
FIGS. 14A-D depict data showing the effect of rhPRG4 on boundary lubrication at a human cornea-eyelid interface (FIG. 14A—static, FIG. 14B—kinetic) and human cornea-PDMS (FIG. 14C—static, FIG. 14D—kinetic) interfaces, of native bovine PRG4 and rhPRG4 at 300 µg/ml in saline, and saline alone. Values are mean±SEM (n=6) with an average normal stress of 14.1±2.2 and 16.9±5.3 (mean±SD) for the cornea-eyelid (AB) and cornea-PDMS (CD) interfaces, respectively. These data illustrate the virtually identical lubricating properties of rhPRG4 and purified native PRG4 in low load lubrication tasks.
Figure 14C:
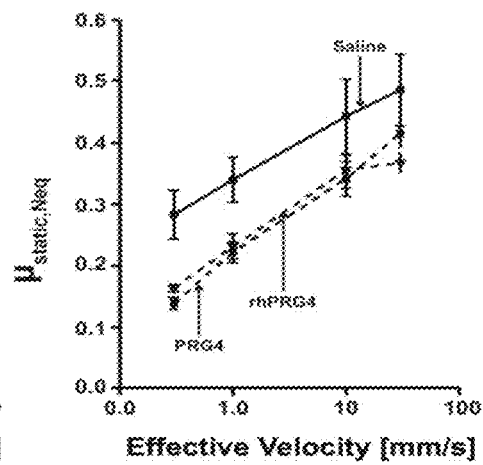
Figure 14B:
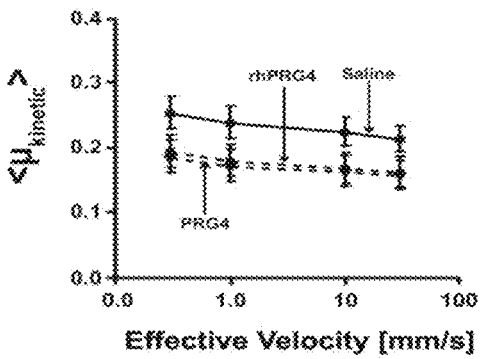
Figure 14D:
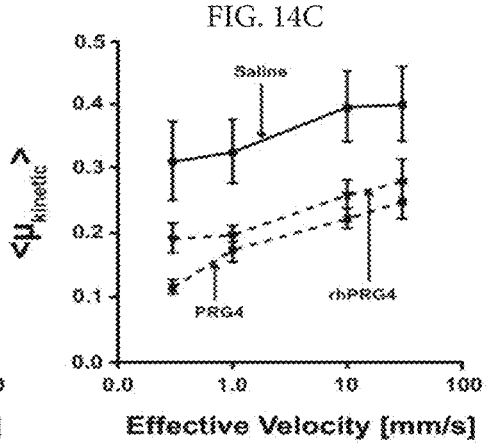

To evaluate the effectiveness of the test lubricants at the two interfaces, static and kinetic friction coefficients were calculated. As illustrated in FIG. 14, both PRG4 and rhPRG4, significantly and similarly, reduced friction at a human cornea—PDMS interface (cf. FIGS. 14C and 14D) and at cornea eyelid interfaces (FIGS. 14A and 14B).

What is claimed is:

1. A recombinant lubricin glycoprotein expressed from a human PRG4 gene in a host cell culture, glycosylation of which is at least 90% core 1 glycosylation.

2. The recombinant lubricin glycoprotein of claim 1, wherein the glycoprotein has a molecular weight of at least 450 kDa.

3. The recombinant lubricin glycoprotein of claim 1, comprising at least 30% by weight glycosidic residues.

4. The recombinant lubricin glycoprotein of claim 1, wherein the lubricin glycoprotein comprises at least 35% by weight glycosidic residues.

5. The recombinant lubricin glycoprotein of claim 1, wherein at least 95% by weight of glycosylation of the lubricin glycoprotein is core 1 glycosylation.

6. The recombinant lubricin glycoprotein of claim 1, wherein at least 99% by weight of glycosylation of the lubricin glycoprotein is core 1 glycosylation.

7. The recombinant lubricin glycoprotein of claim 1, wherein the recombinant human lubricin glycoprotein is monomeric.

8. The recombinant lubricin glycoprotein of claim 1, wherein the recombinant human lubricin glycoprotein is dimeric.

9. The recombinant lubricin glycoprotein of claim 1, the glycosylation of which is at least 95% core 1 glycosylation.

10. The recombinant lubricin glycoprotein of claim 1, the glycosylation of which is at least 99% core 1 glycosylation.

* * * * *

SEQUENCE LISTING

<160> NUMBER OF SEQ ID NOS: 3

<210> SEQ ID NO 1
<211> LENGTH: 1404
<212> TYPE: PRT

<213> ORGANISM: Homo sapiens

<400> SEQUENCE: 1

```
Met Ala Trp Lys Thr Leu Pro Ile Tyr Leu Leu Leu Leu Ser Val
1               5                   10                  15

Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
                35                  40                  45

Asn Cys Gln His Tyr Met Glu Cys Cys Pro Asp Phe Lys Arg Val Cys
            50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                        85                  90                  95

Cys Pro Asp Tyr Glu Ser Phe Cys Ala Glu Val His Asn Pro Thr Ser
                100                 105                 110

Pro Pro Ser Ser Lys Lys Ala Pro Pro Ser Gly Ala Ser Gln Thr
                115                 120                 125

Ile Lys Ser Thr Thr Lys Arg Ser Pro Lys Pro Pro Asn Lys Lys
            130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser Ser
                    165                 170                 175

Ser Thr Ile Arg Lys Ile Lys Ser Ser Lys Asn Ser Ala Ala Asn Arg
                180                 185                 190

Glu Leu Gln Lys Lys Leu Lys Val Lys Asp Asn Lys Lys Asn Arg Thr
            195                 200                 205

Lys Lys Lys Pro Thr Pro Lys Pro Pro Val Val Asp Glu Ala Gly Ser
        210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
                260                 265                 270

Glu Thr Ser Leu Thr Val Asn Lys Glu Thr Thr Val Glu Thr Lys Glu
            275                 280                 285

Thr Thr Thr Thr Asn Lys Gln Thr Ser Thr Asp Gly Lys Glu Lys Thr
        290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
                325                 330                 335

Thr Thr Thr Lys Gly Pro Ala Leu Thr Thr Pro Lys Glu Pro Thr Pro
                340                 345                 350

Thr Thr Pro Lys Glu Pro Ala Ser Thr Thr Pro Lys Glu Pro Thr Pro
            355                 360                 365

Thr Thr Ile Lys Ser Ala Pro Thr Thr Pro Lys Glu Pro Ala Pro Thr
        370                 375                 380

Thr Thr Lys Ser Ala Pro Thr Thr Pro Lys Glu Pro Ala Pro Thr Thr
385                 390                 395                 400
```

-continued

Thr Lys Glu Pro Ala Pro Thr Thr Pro Lys Glu Pro Ala Pro Thr Thr
                        405                 410                 415

Thr Lys Glu Pro Ala Pro Thr Thr Thr Lys Ser Ala Pro Thr Thr Pro
                        420                 425                 430

Lys Glu Pro Ala Pro Thr Thr Pro Lys Lys Pro Ala Pro Thr Thr Pro
                435                 440                 445

Lys Glu Pro Ala Pro Thr Thr Pro Lys Glu Pro Thr Pro Thr Thr Pro
                450                 455                 460

Lys Glu Pro Ala Pro Thr Thr Lys Glu Pro Ala Pro Thr Thr Pro Lys
465                 470                 475                 480

Glu Pro Ala Pro Thr Ala Pro Lys Lys Pro Ala Pro Thr Thr Pro Lys
                485                 490                 495

Glu Pro Ala Pro Thr Thr Pro Lys Glu Pro Ala Pro Thr Thr Thr Lys
                500                 505                 510

Glu Pro Ser Pro Thr Thr Pro Lys Glu Pro Ala Pro Thr Thr Thr Lys
                515                 520                 525

Ser Ala Pro Thr Thr Thr Lys Glu Pro Ala Pro Thr Thr Lys Ser
530                 535                 540

Ala Pro Thr Thr Pro Lys Glu Pro Ser Pro Thr Thr Thr Lys Glu Pro
545                 550                 555                 560

Ala Pro Thr Thr Pro Lys Glu Pro Ala Pro Thr Thr Pro Lys Lys Pro
                565                 570                 575

Ala Pro Thr Thr Pro Lys Glu Pro Ala Pro Thr Thr Pro Lys Glu Pro
                580                 585                 590

Ala Pro Thr Thr Thr Lys Lys Pro Ala Pro Thr Thr Pro Lys Glu Pro
                595                 600                 605

Ala Pro Thr Thr Pro Lys Glu Thr Ala Pro Thr Thr Pro Lys Lys Leu
                610                 615                 620

Thr Pro Thr Thr Pro Glu Lys Leu Ala Pro Thr Thr Pro Glu Lys Pro
625                 630                 635                 640

Ala Pro Thr Thr Pro Glu Glu Leu Ala Pro Thr Thr Pro Glu Glu Pro
                645                 650                 655

Thr Pro Thr Thr Pro Glu Glu Pro Ala Pro Thr Thr Pro Lys Ala Ala
                660                 665                 670

Ala Pro Asn Thr Pro Lys Glu Pro Ala Pro Thr Thr Pro Lys Glu Pro
                675                 680                 685

Ala Pro Thr Thr Pro Lys Glu Pro Ala Pro Thr Thr Pro Lys Glu Thr
                690                 695                 700

Ala Pro Thr Thr Pro Lys Gly Thr Ala Pro Thr Thr Leu Lys Glu Pro
705                 710                 715                 720

Ala Pro Thr Thr Pro Lys Lys Pro Ala Pro Lys Glu Leu Ala Pro Thr
                725                 730                 735

Thr Thr Lys Glu Pro Thr Ser Thr Thr Cys Asp Lys Pro Ala Pro Thr
                740                 745                 750

Thr Pro Lys Gly Thr Ala Pro Thr Thr Pro Lys Glu Pro Ala Pro Thr
                755                 760                 765

Thr Pro Lys Glu Pro Ala Pro Thr Thr Pro Lys Gly Thr Ala Pro Thr
                770                 775                 780

Thr Leu Lys Glu Pro Ala Pro Thr Thr Pro Lys Lys Pro Ala Pro Lys
785                 790                 795                 800

Glu Leu Ala Pro Thr Thr Thr Lys Gly Pro Thr Ser Thr Thr Ser Asp
                805                 810                 815

Lys Pro Ala Pro Thr Thr Pro Lys Glu Thr Ala Pro Thr Thr Pro Lys

```
                820                 825                 830
Glu Pro Ala Pro Thr Thr Pro Lys Lys Pro Ala Pro Thr Thr Pro Glu
            835                 840                 845

Thr Pro Pro Pro Thr Thr Ser Glu Val Ser Thr Pro Thr Thr Thr Lys
850                 855                 860

Glu Pro Thr Thr Ile His Lys Ser Pro Asp Glu Ser Thr Pro Glu Leu
865                 870                 875                 880

Ser Ala Glu Pro Thr Pro Lys Ala Leu Glu Asn Ser Pro Lys Glu Pro
            885                 890                 895

Gly Val Pro Thr Thr Lys Thr Pro Ala Ala Thr Lys Pro Glu Met Thr
            900                 905                 910

Thr Thr Ala Lys Asp Lys Thr Thr Glu Arg Asp Leu Arg Thr Thr Pro
            915                 920                 925

Glu Thr Thr Thr Ala Ala Pro Lys Met Thr Lys Glu Thr Ala Thr Thr
            930                 935                 940

Thr Glu Lys Thr Thr Glu Ser Lys Ile Thr Ala Thr Thr Thr Gln Val
945                 950                 955                 960

Thr Ser Thr Thr Thr Gln Asp Thr Thr Pro Phe Lys Ile Thr Thr Leu
            965                 970                 975

Lys Thr Thr Thr Leu Ala Pro Lys Val Thr Thr Thr Lys Lys Thr Ile
            980                 985                 990

Thr Thr Thr Glu Ile Met Asn Lys  Pro Glu Glu Thr Ala  Lys Pro Lys
            995                 1000                1005

Asp Arg Ala Thr Asn Ser Lys  Ala Thr Thr Pro Lys  Pro Gln Lys
1010                1015                1020

Pro Thr Lys Ala Pro Lys Lys  Pro Thr Ser Thr Lys  Lys Pro Lys
            1025                1030                1035

Thr Met  Pro Arg Val Arg Lys  Pro Lys Thr Thr Pro  Thr Pro Arg
            1040                1045                1050

Lys Met  Thr Ser Thr Met Pro  Glu Leu Asn Pro Thr  Ser Arg Ile
            1055                1060                1065

Ala Glu  Ala Met Leu Gln Thr  Thr Thr Arg Pro Asn  Gln Thr Pro
            1070                1075                1080

Asn Ser  Lys Leu Val Glu Val  Asn Pro Lys Ser Glu  Asp Ala Gly
            1085                1090                1095

Gly Ala  Glu Gly Glu Thr Pro  His Met Leu Leu Arg  Pro His Val
            1100                1105                1110

Phe Met  Pro Glu Val Thr Pro  Asp Met Asp Tyr Leu  Pro Arg Val
            1115                1120                1125

Pro Asn  Gln Gly Ile Ile Ile  Asn Pro Met Leu Ser  Asp Glu Thr
            1130                1135                1140

Asn Ile  Cys Asn Gly Lys Pro  Val Asp Gly Leu Thr  Thr Leu Arg
            1145                1150                1155

Asn Gly  Thr Leu Val Ala Phe  Arg Gly His Tyr Phe  Trp Met Leu
            1160                1165                1170

Ser Pro  Phe Ser Pro Pro Ser  Pro Ala Arg Arg Ile  Thr Glu Val
            1175                1180                1185

Trp Gly  Ile Pro Ser Pro Ile  Asp Thr Val Phe Thr  Arg Cys Asn
            1190                1195                1200

Cys Glu  Gly Lys Thr Phe Phe  Phe Lys Asp Ser Gln  Tyr Trp Arg
            1205                1210                1215

Phe Thr  Asn Asp Ile Lys Asp  Ala Gly Tyr Pro Lys  Pro Ile Phe
            1220                1225                1230
```

```
Lys Gly Phe Gly Gly Leu Thr Gly Gln Ile Val Ala Ala Leu Ser
    1235                1240                1245

Thr Ala Lys Tyr Lys Asn Trp Pro Glu Ser Val Tyr Phe Phe Lys
    1250                1255                1260

Arg Gly Gly Ser Ile Gln Gln Tyr Ile Tyr Lys Gln Glu Pro Val
    1265                1270                1275

Gln Lys Cys Pro Gly Arg Arg Pro Ala Leu Asn Tyr Pro Val Tyr
    1280                1285                1290

Gly Glu Thr Thr Gln Val Arg Arg Arg Phe Glu Arg Ala Ile
    1295                1300                1305

Gly Pro Ser Gln Thr His Thr Ile Arg Ile Gln Tyr Ser Pro Ala
    1310                1315                1320

Arg Leu Ala Tyr Gln Asp Lys Gly Val Leu His Asn Glu Val Lys
    1325                1330                1335

Val Ser Ile Leu Trp Arg Gly Leu Pro Asn Val Val Thr Ser Ala
    1340                1345                1350

Ile Ser Leu Pro Asn Ile Arg Lys Pro Asp Gly Tyr Asp Tyr Tyr
    1355                1360                1365

Ala Phe Ser Lys Asp Gln Tyr Tyr Asn Ile Asp Val Pro Ser Arg
    1370                1375                1380

Thr Ala Arg Ala Ile Thr Thr Arg Ser Gly Gln Thr Leu Ser Lys
    1385                1390                1395

Val Trp Tyr Asn Cys Pro
    1400

<210> SEQ ID NO 2
<211> LENGTH: 5041
<212> TYPE: DNA
<213> ORGANISM: Homo sapiens

<400> SEQUENCE: 2
gcggccgcga ctattcggta cctgaaaaca acgatggcat ggaaaacact tcccatttac     60
ctgttgttgc tgctgtctgt tttcgtgatt cagcaagttt catctcaaga tttatcaagc    120
tgtgcaggga gatgtgggga agggtattct agagatgcca cctgcaactg tgattataac    180
tgtcaacact acatggagtg ctgccctgat ttcaagagag tctgcactgc ggagctttcc    240
tgtaaaggcc gctgctttga gtccttcgag agagggaggg agtgtgactg cgacgcccaa    300
tgtaagaagt atgacaagtg ctgtcccgat tatgagagtt tctgtgcaga agtgcataat    360
cccacatcac caccatcttc aaagaaagca cctccacctt caggagcatc tcaaaccatc    420
aaatcaacaa ccaaacgttc acccaaacca ccaaacaaga gaagactaa gaaagttata    480 gaatcagagg aaataacaga gaacattct gtttctgaaa atcaagagtc ctcctcctcc    540
tcctcctctt cctcttcttc ttcaacaatt tggaaaatca agtcttccaa aaattcagct    600
gctaatagag aattacagaa gaaactcaaa gtaaaagata caagaagaa cagaactaaa    660 aagaaaccta cccccaaacc accagttgta gatgaagctg gaagtggatt ggacaatggt    720
gacttcaagg tcacaactcc tgacacgtct accaccaac acaataaagt cagcacatct    780
cccaagatca aacagcaaa accaataaat cccagaccca gtcttccacc taattctgat    840
acatctaaag agacgtcttt gacagtgaat aaagagacaa cagttgaaac taaagaaact    900
actacaacaa ataaacagac ttcaactgat ggaaaagaga agactacttc cgctaaagag    960
acacaaagta tagagaaaac atctgctaaa gatttagcac ccacatctaa agtgctggct   1020
```

```
aaacctacac ccaaagctga aactacaacc aaaggccctg ctctcaccac tcccaaggag      1080
cccacgccca ccactcccaa ggagcctgca tctaccacac ccaaagagcc cacacctacc      1140
accatcaagt ctgcacccac cacccccaag gagcctgcac ccaccaccac caagtctgca      1200
cccaccactc ccaaggagcc tgcacccacc accaccaagg agcctgcacc caccactccc      1260
aaggagcctg cacccaccac caccaaggag cctgcaccca ccaccaa gtctgcaccc         1320
accactccca aggagcctgc acccaccacc cccaagaagc tgccccaac taccccaag        1380
gagcctgcac ccaccactcc caaggagcct acacccacca ctcccaagga gcctgcaccc      1440
accaccaagg agcctgcacc caccactccc aagagcctg cacccactgc cccaagaag        1500
cctgccccaa ctaccccaa ggagcctgca cccaccactc caaggagcc tgcacccacc        1560
accaccaagg agccttcacc caccactccc aaggagcctg cacccaccac caccaagtct      1620
gcacccacca ctaccaagga gcctgcaccc accactacca agtctgcacc caccactccc      1680
aaggagcctt cacccaccac caccaaggag cctgcaccca ccactcccaa ggagcctgca      1740
cccaccaccc caagaagcc tgccccaact accccaagg agcctgcacc caccactccc        1800
aaggaacctg cacccaccac caccaagaag cctgcaccca ccgctcccaa agagcctgcc      1860
ccaactaccc ccaaggagac tgcacccacc acccccaaga agctcacgcc caccacccc       1920
gagaagctcg cacccaccac ccctgagaag cccgcaccca ccaccctga ggagctcgca       1980
cccaccaccc ctgaggagcc cacacccacc acccctgagg agcctgctcc caccactccc      2040
aaggcagcgg ctcccaacac ccctaaggag cctgctccaa ctacccctaa ggagcctgct      2100
ccaactaccc ctaaggagcc tgctccaact accccctaagg agactgctcc aactaccccct   2160
aaagggactg ctccaactac cctcaaggaa cctgcaccca ctactcccaa gaagcctgcc      2220
cccaaggagc ttgcacccac caccaccaag gagcccacat ccaccacctc tgacaagccc      2280
gctccaacta ccctaaggg actgctccaa ctaccccta aggagcctgc tccaactacc        2340
cctaaggagc ctgctccaac tacccctaag gggactgctc caactaccct caaggaacct      2400
gcacccacta ctcccaagaa gcctgccccc aaggagcttg cacccaccac caccaagggg      2460
cccacatcca cccacctctga caagcctgct ccaactacac ctaaggagac tgctccaact    2520
accccccaagg agcctgcacc cactacccc caagaagcctg ctccaactac tcctgagaca     2580
cctcctccaa ccacttcaga ggtctctact ccaactacca ccaaggagcc taccactatc     2640
cacaaaagcc ctgatgaatc aactcctgag ctttctgcag aacccacacc aaaagctctt     2700
gaaaacagtc ccaaggaacc tggtgtacct acaactaaga ctcctgcagc gactaaacct     2760
gaaatgacta caacagctaa agacaagaca acagaaagag acttacgtac tacacctgaa     2820
actacaactg ctgcacctaa gatgacaaaa gagacagcaa ctacaacaga aaaaactacc     2880
gaatccaaaa taacagctac aaccacacaa gtaacatcta ccacaactca agataccaca     2940
ccattcaaaa ttactactct taaaacaact actcttgcac ccaaagtaac tacaacaaaa    3000
aagacaatta ctaccactga gattatgaac aaacctgaag aaacagctaa accaaaagac     3060
agagctacta attctaaagc gacaactcct aaacctcaaa agccaaccaa agcacccaaa     3120
aaacccactt ctaccaaaaa gccaaaaaca atgcctagg tgagaaaacc aaagacgaca     3180
ccaactcccc gcaagatgac atcaacaatg ccagaattga accctacctc aagaatagca     3240
gaagccatgc tccaaaccac caccagacct aaccaaactc caaactccaa actagttgaa     3300
gtaaatccaa agagtgaaga tgcaggtggt gctgaaggag aaacacctca tatgcttctc     3360
aggccccatg tgttcatgcc tgaagttact cccgacatgg attacttacc gagagtaccc     3420
```

```
aatcaaggca ttatcatcaa tcccatgctt tccgatgaga ccaatatatg caatggtaag    3480
ccagtagatg gactgactac tttgcgcaat gggacattag ttgcattccg aggtcattat    3540
ttctggatgc taagtccatt cagtccacca tctccagctc gcagaattac tgaagtttgg    3600
ggtattcctt cccccattga tactgttttt actaggtgca actgtgaagg aaaaactttc    3660
ttctttaagg attctcagta ctggcgtttt accaatgata taaaagatgc agggtacccc    3720
aaaccaattt tcaaaggatt tggaggacta actggacaaa tagtggcagc gctttcaaca    3780
gctaaatata agaactggcc tgaatctgtg tattttttca agagaggtgg cagcattcag    3840
cagtatattt ataaacagga acctgtacag aagtgccctg aagaaggcc tgctctaaat     3900 tatccagtgt atggagaaat gacacaggtt aggagacgtc gctttgaacg tgctatagga    3960
ccttctcaaa cacacaccat cagaattcaa tattcacctg ccagactggc ttatcaagac    4020
aaaggtgtcc ttcataatga agttaaagtg agtatactgt ggagaggact tccaaatgtg    4080
gttacctcag ctatatcact gcccaacatc agaaaacctg acggctatga ttactatgcc    4140
ttttctaaag atcaatacta taacattgat gtgcctagta aacagcaag agcaattact     4200 actcgttctg ggcagacctt atccaaagtc tggtacaact gtccttagac tgatgagcaa    4260
aggaggagtc aactaatgaa gaaatgaata ataaattttg acactgaaaa acattttatt    4320
aataaagaat attgacatga gtataccagt ttatatataa aaatgttttt aaacttgaca    4380
atcattacac taaaacagat ttgataatct tattcacagt tgttattgtt tacagaccat    4440
ttaattaata tttcctctgt ttattcctcc tctccctccc attgcatggc tcacacctgt    4500
aaaagaaaaa agaatcaaat tgaatatatc ttttaagaat tcaaaactag tgtattcact    4560
taccctagtt cattataaaa aatatctagg cattgtggat ataaaactgt tgggtattct    4620
acaacttcaa tggaaattat tacaagcaga ttaatccctc tttttgtgac acaagtacaa    4680
tctaaaagtt atattggaaa acatggaaat attaaaattt tacacttta ctagctaaaa     4740 cataatcaca aagctttatc gtgttgtata aaaaaattaa caatataatg gcaataggta    4800
gagatacaac aaatgaatat aacactataa cacttcatat tttccaaatc ttaatttgga    4860
tttaaggaag aaatcaataa atataaaata taagcacata tttattatat atctaaggta    4920
tacaaatctg tctacatgaa gtttacagat tggtaaatat cacctgctca acatgtaatt    4980
atttaataaa actttggaac attaaaaaaa taaattggag gcttaaaaaa aaaaaaaaa    5040 a                                                                   5041

<210> SEQ ID NO 3
<211> LENGTH: 7
<212> TYPE: PRT
<213> ORGANISM: Homo sapiens

<400> SEQUENCE: 3

Lys Glu Pro Ala Pro Thr Thr
1               5
```